(12) United States Patent
Lindmark et al.

(10) Patent No.: US 11,382,903 B2
(45) Date of Patent: Jul. 12, 2022

(54) CANCER THERAPY

(71) Applicant: Aslan Pharmaceuticals Pte. Ltd., Singapore (SG)

(72) Inventors: Bertil Lindmark, Singapore (SG); Ann Gee Lisa Ooi, Singapore (SG); Mark Thomas McHale, Singapore (SG)

(73) Assignee: Aslan Pharmaceuticals Pte. Ltd., Singapore (SG)

(*) Notice: Subject to any disclaimer, the term of this patent is extended or adjusted under 35 U.S.C. 154(b) by 0 days.

(21) Appl. No.: 16/154,422

(22) Filed: Oct. 8, 2018

(65) Prior Publication Data

US 2019/0038610 A1  Feb. 7, 2019

Related U.S. Application Data

(63) Continuation-in-part of application No. PCT/SG2018/050092, filed on Mar. 1, 2018.

(30) Foreign Application Priority Data

Mar. 2, 2017 (GB) .................................. 1703453
Mar. 3, 2017 (SG) ........................... 10201701753P
May 31, 2017 (SG) ........................... 10201704475Y
Aug. 23, 2017 (SG) ........................... 10201706887Q

(51) Int. Cl.
| | |
|---|---|
| A61K 31/4418 | (2006.01) |
| A61P 35/02 | (2006.01) |
| A61K 31/505 | (2006.01) |
| A61K 45/06 | (2006.01) |
| A61K 31/075 | (2006.01) |
| A61K 31/4545 | (2006.01) |
| A61K 31/502 | (2006.01) |
| A61K 31/517 | (2006.01) |
| A61K 31/553 | (2006.01) |

(52) U.S. Cl.
CPC ........ *A61K 31/4418* (2013.01); *A61K 31/505* (2013.01); *A61K 45/06* (2013.01); *A61P 35/02* (2018.01); *A61K 31/075* (2013.01); *A61K 31/4545* (2013.01); *A61K 31/502* (2013.01); *A61K 31/517* (2013.01); *A61K 31/553* (2013.01); *A61K 2300/00* (2013.01)

(58) Field of Classification Search
CPC ............. A61K 31/505; A61K 31/075; A61K 31/4545; A61K 31/502; A61K 31/517; A61K 31/164; A61K 31/201; A61K 31/4418; A61K 31/4745; A61K 31/4995; A61K 31/5377; A61K 31/553; A61K 31/704; A61K 45/06; A61K 2300/00; A61P 35/02
See application file for complete search history.

(56) References Cited

U.S. PATENT DOCUMENTS

2005/0245466 A1* 11/2005 Jenkins .................. A61K 31/12
  514/27
2015/0182504 A1  7/2015 Pan et al.

FOREIGN PATENT DOCUMENTS

| EP | 2 444 088 A1 | 4/2012 |
|---|---|---|
| EP | 2 594 271 A1 | 5/2013 |
| WO | 2008/077639 A1 | 7/2008 |
| WO | 2010/128050 A2 | 11/2010 |
| WO | 2012/052179 A1 | 4/2012 |
| WO | 2015/154820 A1 | 10/2015 |
| WO | 2016/198663 A1 | 12/2016 |
| WO | 2017/037292 A1 | 3/2017 |
| WO | 2018/136009 A1 | 7/2018 |
| WO | 2018/136010 A1 | 7/2018 |
| WO | 2018/222134 A1 | 12/2018 |
| WO | 2018/222135 A1 | 12/2018 |

OTHER PUBLICATIONS

Sykes et al. (Cell (2016), vol. 167, pp. 171-186). (Year: 2016).*
Minderman et al. (Cancer Chemother Pharmacol (2006), vol. 57, pp. 73-83) (Year: 2006).*
Pommier et al. (Prog Nucleic Acid Res Mol Biol (2006), vol. 81, pp. 179-229). (Year: 2006).*
International Search Report, International Application No. PCT/SG2018/050092 (published under WO 2018/160138), 2 pages (dated Jun. 20, 2018).
Abdullah et al, "Benzimidazole derivatives as potential dual inhibitors for PARP-1 and DHODH," Bioorganic and Medicinal Chemistry, vol. 23, No. 15, Aug. 1, 2015, 4669-4680.
Brown et al, "Adaptive Reprogramming of De Novo Pyrimidine Synthesis Is a Metabolic Vulnerability in Triple Negative Breast Cancer," Cancer Discovery, vol. 7, No. 4, Apr. 2017, 391-399.
Fairus et al, "Dihydroorotate dehydrogenase (DHODH) inhibitors affect ATP depletion, endogenous ROS and mediate S-phase arrest in breast cancer cells," Biochimie, vol. 135, Apr. 2017, 154-163.
Jiang et al, "Abstract P2-09-21: Teriflunomide, an immunomodulatory drug, exerts anticancer activity in triple-negative breast cancer (TNBC) cells via modulation of multiple cell signal pathways," Cancer Research, vol. 73, No. 24 Suppl, Dec. 2013.
Mathur et al, "PTEN Regulates Glutamine Flux to Pyrimidine Synthesis and Sensitivity to Dihydroorotate Dehydrogenase Inhibition," Cancer Discovery, vol. 7, No. 4, Apr. 2017, 380-390.
Baumann et al., "Dihydroorotate dehydrogenase inhibitor A771726 (leflunomide) induces apoptosis and diminshes proliferation of multiple myeloma cells," Molecular Cancer Therapy, vol. 8, No. 2, pp. 366-375 (Feb. 2009; published online Jan. 27, 2009).

(Continued)

*Primary Examiner* — Umamaheswari Ramachandran
(74) *Attorney, Agent, or Firm* — Prismatic Law Group, PLLC; Ron Kamis

(57) ABSTRACT

A method of treating haematological cancer with a therapy comprising a DHODH inhibitor. Also provided is a combination therapy comprising a pan-HER inhibitor and a DHODH inhibitor for treating a haematological cancer.

13 Claims, 16 Drawing Sheets

(56) References Cited

OTHER PUBLICATIONS

Chemotherapy, vol. 34, No. 12, pp. 1308-1309, 1306 (Dec. 1986).
Lewis et al., "Development of ML390: A Human DHODH Inhibitor That Induces Differentiation in Acute Myeloid Leukemia," ACS Medical Chemistry Letters, vol. 7, No. 12, pp. 1112-1117 (Sep. 28, 2016).
Ma et al., "A new target for differentiation therapy in AML," Cell Research, vol. 27, pp. 9-10 (2017; published online Nov. 11, 2016).
Rui Xiong et al, BioRxiv, Mar. 12, 2020, XP055740305.
Boschi et al, Eur J. Med Chem, vol. 183, Sep. 12, 2019 111681-.
Stegmann et al, BioRxvi, Jun. 28, 2021, XP0558683440.

* cited by examiner

DMSO CONTROL

ASLAN003 100nM

DMSO Control

ASLAN003 100nM

DMSO CONTROL

ASLAN003 500nM

DMSO CONTROL

ASLAN003 1µM

DMSO control

ASLAN003 4000 nM

DMSO control

ASLAN003 4000 nM

CANCER THERAPY

CROSS-REFERENCE TO RELATED APPLICATIONS

This application is a continuation-in-part of International Patent Application No. PCT/SG2018/050092 filed Mar. 1, 2018, which claims priority to British Patent Application No. 1703453.9 filed Mar. 2, 2017, Singapore Patent Application No. 10201701753P filed Mar. 3, 2017, Singapore Patent Application No. 10201704475Y filed May 31, 2017, and Singapore Patent Application No. 10201706887Q filed Aug. 23, 2017, the content of each of which applications is incorporated herein by reference.

The present disclosure relates to a method of treating haematological cancer with a therapy comprising a DHODH inhibitor.

BACKGROUND

Haematological cancers are a group of cancers that originate in blood-forming tissues, such as in immune cells, lymphatic system or in the bone marrow. There are 3 principal types of haematological cancers: leukaemias, which are caused by the rapid production of abnormal white blood cells; lymphomas which are caused by abnormal lymphoma cells, and myelomas, which is a cancer of the plasma cells. The American Cancer society estimates that in 2017, there were approximately 62,130, 30,280 and 80,500 new leukaemia, myeloma and lymphoma cases, respectively within the US alone (Cancer Facts & Figures 2017, American Cancer Society). Five-year survival rates for these cancers has steadily improved over time to about 63%, 73% and 50% for leukaemia, myeloma and lymphoma patients respectively, who were first diagnosed in 2006-2012 (SEER program Cancer Statistics Review (CSR) 1975-2013). Nonetheless, despite improvements in the treatment and diagnosis of haemotological cancers, these cancers still present a significant healthcare burden.

Leukaemias can be further divided into 4 main types: acute lymphoblastic leukaemia (ALL), acute myeloid leukaemia (AML), chronic lymphocytic leukaemia (CLL), and chronic myeloid leukaemia (CML). AML and CML are both myeloproliferative neoplasms—in AML the body produces an excess number of immature white blood cells in the bone marrow, whilst in CML the body produces too many mature white blood cells.

AML is the most common malignant myeloid disorder in adults with an annual incidence of about 3.8 per 100,000 individuals. Left untreated, AML typically results in bone marrow failure, which leads to fatal infections, bleeding or organ infiltration, often within weeks to months of diagnosis. Standard chemotherapy for AML includes cytosine arabinoside (ara-c) in combination with an anthracycline, for example daunorubicin or a nucleoside analogue fludarabine. Although chemotherapy can effectively induce remission in many AML patients, the risk of relapse is high. As a consequence, the identification of novel therapies to treat AML is crucial. In this respect, various new antibody mediated therapies which target CD47 (which has been shown to be a poor prognostic factor in AML) and small molecule inhibitors that target signaling pathways such as Hedgehog and Wnt are being developed.

Myelodysplastic syndrome (MDS) is a group of blood cancers in which immature blood cells in the blood marrow fail to mature and become cancerous. The disease has an annual incidence of around 7 per 100,000 individuals and the usual age of onset is 70 years old. Treatment options include blood transfusions to replace the red blood, white blood or platelets in patients with MDS and chemotherapy with hypomethylating agents such as 5-azacytidine and decitabine. The typical survival rate is poor, with most patients surviving 2.5 years after diagnosis.

Hence, there is an urgent requirement for further novel therapies to treat haematological cancers, such as AML and MDS.

SUMMARY OF THE DISCLOSURE

Dihydroorotate dehydrogenase inhibitors (DHODH inhibitors) are thought to be useful in the treatment of rheumatoid arthritis. Examples of known DHODH inhibitors include leflunomide or teriflunomide. However, the present inventors believe that the DHODH inhibitor 2-(3,5-difluoro-3'methoxybiphenyl-4-ylamino)nicotinic acid (also known as ASLAN003) or a pharmaceutically acceptable salt thereof, is also useful in the treatment of haematological disorders, for example leukaemias, such as AML or MDS.

Thus in a first aspect the present disclosure provides a method of treating a haematological cancer patient comprising administering a therapeutically effect amount of a DHODH inhibitor 2-(3,5-difluoro-3'methoxybiphenyl-4-ylamino)nicotinic acid or a pharmaceutically acceptable salt thereof.

Also provided is a method of treating cancer by killing cancer cells by apoptosis, said method comprising administering a therapeutically effective amount of DHODH inhibitor 2-(3,5-difluoro-3'methoxybiphenyl-4-ylamino) nicotinic acid or a pharmaceutically acceptable salt thereof.

In one embodiment the DHODH of the present disclosure does not kill cancers by a necrotic mechanism.

In one embodiment the haematological cancer is selected from myeloma, lymphoma, leukaemia, such as acute myeloid leukaemia (AML), chronic myeloproliferative disease, monoclonal gammopathy of uncertain significance, myelodysplastic syndrome and amyloidosis.

In one embodiment, the haematological cancer is MDS.

In one embodiment the myeloma is selected from multiple myeloma, amyloidosis and plasmacytoma.

In one embodiment the myeloma is selected from monoclonal gammopathy of undetermined significance, asymoptomatic myeloman, symptomatic myeloma and Kahler's disease.

In one embodiment the lymphoma is selected from anaplastic large cell lymphoma, Burkitt lymphoma, Burkitt-like lymphoma, cutaneous T-cell lymphoma, diffuse large B-cell lymphoma, diffuse large B-cell lymphoma, lymphoblastic lymphoma, MALT lymphoma, mantle cell lymphoma, mediastinal large B-cell lymphoma, nodal marginal zone B-cell lymphoma, small lymphocytic lymphoma, thyroid lymphoma, and Waldenstrom's macroglobulinaemia.

In one embodiment the chronic myeloproliferative disease is selected from essential thrombocythaemia, chronic idiopathic myelofibrosis, and polycythaemia rubra vera.

In one embodiment the leukaemia is selected from acute myeloid leukaemia (AML), hairy cell leukaemia, acute lymphoblastic leukaemia, and chronic lymphoblastic leukaemia.

In one embodiment the haematological cancer is acute myeloid leukaemia (AML).

In one embodiment the DHODH inhibitor provides anti-cancer efficacy via induction of p53.

In one embodiment the DHODH of the present disclosure is more potent than known DHODH inhibitors.

In one embodiment the DHODH of the present disclosure drives blast cell differentiation, for example measured by induction of CD11b and/or CD14.

In one embodiment the DHODH inhibitor is administered orally, for example once daily.

In one embodiment the treatment according to the present disclosure prolongs survival of the patient, for example 1 to 60 months.

Also provided is 2-(3,5-difluoro-3'methoxybiphenyl-4-ylamino)nicotinic acid or a pharmaceutically acceptable salt thereof for use in the treatment of a haematological cancer, in particular a haematological cancer disclosed herein, such as AML.

Also provided is 2-(3,5-difluoro-3'methoxybiphenyl-4-ylamino)nicotinic acid or a pharmaceutically acceptable salt thereof for use in the manufacture of a medicament for the treatment of a haematological cancer, in particular a haematological cancer disclosed herein, such as AML or MDS.

In a further aspect there is provided use of a DHODH inhibitor 2-(3,5-difluoro-3'methoxybiphenyl-4-ylamino) nicotinic acid or a pharmaceutically acceptable salt in the manufacture of a combination therapy for the treatment of haematological cancer, in particular a haematological cancer disclosed herein, such as AML or MDS.

Also provided is use of a pan-HER inhibitor (such as R)—N4-[3-Chloro-4-(thiazol2-ylmethoxy)-phenyl]-N6-(4-methyl-4,5-dihydro-oxazol-2-yl)-quinazoline-4,6-diamine or a pharmaceutically acceptable salt thereof) and a DHODH inhibitor 2-(3,5-difluoro-3'methoxybiphenyl-4-ylamino)nicotinic acid or a pharmaceutically acceptable salt in the manufacture of a combination therapy for the treatment of a haematological cancer, in particular a haematological cancer disclosed herein, such as AML or MDS.

In one embodiment the therapy of the present disclosure continues for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 months or more.

(R)—N4-[3-Chloro-4-(thiazol2-ylmethoxy)-phenyl]-N6-(4-methyl-4,5-dihydro-oxazol-2-yl)-quinazoline-4,6-diamine is also known as Varlitinib.

In one embodiment Varlitinib is administered in a 28 day cycle. In one embodiment dosing of the Varlitinib component therapy continues for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 months or more.

The Paragraphs below provide more detail in relation of the present disclosure:

1. A method of treating a haematological cancer comprising administering a therapeutically effect amount of a DHODH inhibitor 2-(3,5-difluoro-3'methoxybiphenyl-4-ylamino)nicotinic acid or a pharmaceutically acceptable salt thereof.
2. A method of treatment according to paragraph 1, wherein the haematological cancer is selected from myeloma, lymphoma, Leukaemia, chronic myeloproliferative disease, monoclonal gammopathy of uncertain significance, myelodysplastic syndrome (MDS), plasma exchange amyloidosis and plasmacytoma.
3. A method of treatment according to paragraph 2, wherein the haematological cancer is myeloma.
4. A method of treatment according to paragraph 2 or 3, wherein the haematological cancer is lymphoma.
5. A method of treatment according paragraph 4, wherein the lymphoma is selected from Hodgkin's lymphoma, and non-Hodgkin's lymphoma.
6. A method of treatment according to any one of paragraphs 2 to 5, wherein the lymphoma is independently selected from anaplastic large cell lymphoma, angioimmunoblastic lymphoma, Burkitt lymphoma, Burkitt-like lymphoma, blastic NK-cell lymphoma, cutaneous T-cell lymphoma, diffuse large B-cell lymphoma, diffuse large B-cell lymphoma, lymphoblastic lymphoma, MALT lymphoma, mantle cell lymphoma, mediastinal large B-cell lymphoma, nodal marginal zone B-cell lymphoma, small lymphocytic lymphoma, thyroid lymphoma, follicular lymphoma, Waldenstrom's macroglobulinaemia and combinations thereof.
7. A method of treatment according to any one of paragraphs 2 to 6, wherein the haematological cancer is chronic myeloproliferative disease.
8. A method of treatment according to any one of paragraphs 2 to 7, wherein the chronic myeloproliferative disease is selected from essential thrombocythaemia, chronic idiopathic myelofibrosis, and polycythaemia rubra vera.
9. A method of treatment according to any one of paragraphs 2 to 8, wherein the haematological cancer is leukaemia.
10. A method of treatment according to paragraphs 9, wherein the leukaemia is independently selected from AML (acute myeloid leukaemia), ALL (acute lymphoblastic leukaemia), CML (chronic myeloid leukaemia) and CLL (chronic lymphocytic leukaemia) and combinations thereof.
11. A method of treatment according to paragraph 8 or 9, wherein the leukaemia is selected from hairy cell leukaemia, acute lymphoblastic leukaemia, and chronic lymphoblastic leukaemia.
12. A method of treatment according to any one of paragraph 9 to 11, wherein the leukaemia is independently selected from acute lymphoblastic leukaemia, chronic lymphoblastic leukaemia, acute myelogenous leukaemia, chronic myelogenous leukaemia, hairy cell leukaemia, T-cell prolymphocytic leukaemia, large granular lymphocytic leukaemia, adult T-cell leukaemia, clonal eosinophilias, T-cell granular leukaemia, NK-cell leukaemia, adult T-cell leukaemia and combinations thereof.
13. A method according to paragraph 12, wherein the leukaemia is AML.
14. A method according to paragraph 12, wherein the leukaemia is ALL.
15. A method according to paragraph 12, wherein the leukaemia is CML.
16. A method according to paragraph 12, wherein the leukaemia is CLL.
17. A method according to paragraph 1, wherein the haematological cancer is MDS.
18. A method of treatment according to any one of paragraphs 1 to 17, wherein the DHODH inhibitor is employed in a combination therapy with a second therapy.
19. A method of treatment according to paragraph 17 wherein the second therapy is an inhibitor of DNA repair.
20. A method of treatment according to paragraph 18 or 19 wherein the inhibitor is a small molecule therapy.
21. A method of treatment according to paragraph 19 or 20, wherein the inhibitor mechanism is via the base excision repair pathway.
22. A method of treatment according to claim 21, wherein the inhibitor's target is independently selected from APE1, Pol β, FEN1, and PARP.

23. A method of treatment according to paragraph 21 or 22, wherein the inhibitor is selected from TRC102, (2E)-2-[(4,5-Dimethoxy-2-methyl-3,6-dioxo-1,4-cyclohexadien-1-yl)methylene]-undecanoic acid [also known as E3330], NCS-666715 and NSC-124854, 8-oxoguanine, tanespirmycin, luminespib, alvespimycin, genetespib, retaspimycin, 6-Amino-8-[(6-iodo-1,3-benzodioxol-5-yl)thio]-N-(1-methylethyl)-9H-purine-9-propanamine (PU-H71), 4-[2-carbamoyl-5-[6,6-dimethyl-4-oxo-3-(trifluoromethyl)-5,7-dihydroindazol-1-yl]anilino]cyclohexyl] 2-aminoacetate (SNX-5422), luminespib (resorcyinylic), 2-(2-ethyl-3,5-dihydroxy-6-(3-methoxy-4-(2-morpholinoethoxy)benzoyl)phenyl)-N,N-bis(2-methoxyethyl)acetamide (KW-2478), AT13387, 5,6-bis((E)-benzylideneamino)-2-thioxo-2,3-dihydropyrimidin-4(1H)-one (SCR7) and combinations of two or more of the same.

24. A method of treatment according to any one of paragraphs 21 to 23, wherein the inhibitor is a PARP inhibitor, such as a PARP-1 and/or PARP-2 inhibitor.

25. A method of treatment according to paragraph 24, wherein the PARP inhibitor is independently selected from olaparib, rucaparib, niraparib, iniparib, talazoparib, veliparib, CEP9722, E7016, BGB-290, AZD-2461, 3-aminobenzamide and combinations thereof.

26. A method of treatment according to any one of paragraphs 19 to 25 wherein the inhibitor mechanism is via the mismatch repair pathway.

27. A method of treatment according to any one of paragraphs 19 to 26, wherein the inhibitor mechanism is via the nucleotide excision pathway.

28. A method of treatment according to paragraph 27, wherein the inhibitor is independently selected from 7-hydroxystaurosporine [UCN-01], trabectedin, MCI13E, NERI01 and combinations of two or more of the same.

29. A method of treatment according to any one of paragraphs 19 to 28, wherein the inhibitor mechanism is via the double stranded break repair pathway.

30. A method of treatment according to paragraph 29, wherein the inhibitor mechanism is via the non-homologous end joining pathway.

31. A method of treatment according to paragraph 29 or 30, wherein the inhibitor is via the homologous recombination pathway.

32. A method of treatment according to any one of paragraphs 18 to 31, wherein the therapy is a topoisomerase inhibitor, such as topoisomerase I and/or II inhibitor.

33. A method of treatment according to paragraph 32, wherein the topoisomerase inhibitor is independently selected from irinotecan, topotecan, camptothecin lamellarin D and combinations thereof.

34. A method of treatment according to paragraph 32 or 33, wherein the topoisomerase inhibitor is independently selected from etoposide (VP-16), teniposide, doxorubicin, daunorubicin, mitoxantrone, amsacrine, ellipticines, aurintricarboxylic acid, 3-Hydroxy-2-[(1R)-6-isopropenyl-3-methyl-cyclohex-2-en-1-yl]-5-pentyl-1,4-benzoquinone (HU-331) and combinations thereof.

35. A method according to any one of paragraphs 18 to 34, wherein the second therapy is an mTor inhibitor, for example everolimus (RAD001), WYE-354, KU-0063794, papamycin (Sirolimus), Temsirolimus, Deforolimus (MK-8669), AZD8055 and BEZ235 (NVP-BEZ235).

36. A method according to any one of paragraphs 18 to 35, wherein the second therapy is a MEK inhibitor, for example AS703026, CI-1040 (PD184352), AZD6244 (Selumetinib), PD318088, PD0325901, AZD8330, PD98059, U0126-EtOH, BIX 02189 or BIX 02188.

37. A method according to any one of paragraphs 18 to 36, wherein the second therapy is an AKT inhibitor, for example MK-2206 and AT7867.

38. A method according to any one of paragraphs 18 to 37, wherein the second therapy is an aurora kinase inhibitor, for example Aurora A Inhibitor I, VX-680, AZD1152-HQPA (Barasertib), SNS314 Mesylate, PHA-680632, ZM-447439, CCT129202 and Hesperadin.

39. A method according to any one of paragraphs 18 to 38, wherein the second therapy is a p38 inhibitor, for example as disclosed in WO2010/038086, such as N-[4-({4-[3-(3-tert-Butyl-1-p-tolyl-1H-pyrazol-5yl)ureido]naphthalen-1-yloxy}methyl)pyridin-2-yl]-2-methoxyacetamide.

40. A method according to any one of claims 1 to 39, wherein the haematological cancer therapy further comprises a pan-HER inhibitor, for example (R)—N4-[3-Chloro-4-(thiazol2-ylmethoxy)-phenyl]-N6-(4-methyl-4,5-dihydro-oxazol-2-yl)-quinazoline-4,6-diamine or a pharmaceutically acceptable salt thereof.

41. A method according to paragraph 40, wherein the pan-HER inhibitor is administered parenterally.

42. A method according to paragraph 40, wherein the pan-HER inhibitor is administered orally.

43. A method according to paragraph 42, wherein the pan-HER inhibitor is administered bi-daily.

44. A method according to paragraph 42 or 43, wherein each dose of the pan-HER inhibitor is in the range 100 to 900 mg, such as 200, 300, 400, 500, 600, 700, 800 mg.

45. A method according to paragraph 44, wherein each dose is in the range 300 to 500 mg, such as 400 mg.

46. A method according to any one of paragraphs 1 to 45, wherein the DHODH inhibitor provides anticancer efficacy via induction of p53.

47. A method according to any one of paragraphs 1 to 46, wherein the DHODH inhibitor is administered orally, for example once daily.

48. A 2-(3,5-difluoro-3'methoxybiphenyl-4-ylamino)nicotinic acid or a pharmaceutically acceptable salt thereof for use in the treatment of a haematological cancer, for example AML or MDS.

49. A combination therapy comprising a pan-HER inhibitor (such as (R)—N4-[3-Chloro-4-(thiazol2-ylmethoxy)-phenyl]-N6-(4-methyl-4,5-dihydro-oxazol-2-yl)-quinazoline-4,6-diamine or a pharmaceutically acceptable salt thereof) and a DHODH inhibitor 2-(3,5-difluoro-3'methoxybiphenyl-4-ylamino)nicotinic acid or a pharmaceutically acceptable salt for use in the treatment of a haematological cancer, such as AML or MDS.

50. Use of a DHODH inhibitor 2-(3,5-difluoro-3'methoxybiphenyl-4-ylamino)nicotinic acid or a pharmaceutically acceptable salt in the manufacture of a therapy for the treatment of haematological cancer, in particular a haematological cancer disclosed herein, in particular AML or MDS.

51. Use of a HER inhibitor (such as (R)—N4-[3-Chloro-4-(thiazol2-ylmethoxy)-phenyl]-N6-(4-methyl-4,5-dihydro-oxazol-2-yl)-quinazoline-4,6-diamine or a pharmaceutically acceptable salt thereof) and a DHODH inhibitor 2-(3,5-difluoro-3'methoxybiphenyl-4-ylamino)nicotinic acid or a pharmaceutically acceptable salt in the manufacture of a combination therapy for the treatment of a haematological cancer, in particular a haematological cancer disclosed herein, such as a AML or MDS.

The disclosure also extends to use of the DHODH inhibitor according to any one of paragraphs 1 to 50 for use in the treatment of a haematological cancer, in particular as described herein, such as AML or MDS.

The disclosure further provides use of the DHODH inhibitor according to any one of paragraphs 1 to 45, in the manufacture of a medicament for the treatment of a haematological cancer, in particular as described herein.

DHODH is a key enzyme in the production of uridine, which is a central building block in the cell. Whilst not wishing to be bound by theory it may be that the DHODH inhibitor is able to upregulate p53 based apoptosis. The up-regulation of p53 (which may lead to cell cycle arrest and at higher levels of p 53, to apoptosis) is likely to occur via mechanisms sensing the levels of intracellular uridine, and then facilitating a series of reactions leading to stabilisation of p53, and increasing its concentration.

Furthermore, the present inventors have established that the DHODH inhibitor 2-(3,5-difluoro-3'methoxybiphenyl-4-ylamino) nicotinic acid or a pharmaceutically acceptable salt thereof is particularly advantageous for use in the treatment of haematological cancers because it kills the cancer cells via apoptosis, and does not involve necrotic cell death.

Necrosis is a form of cell injury which results in premature death of cells in living tissue by autolysis (i.e. destruction of the cell through the action of its own enzymes). Necrosis is caused by factors external to the cell or tissue, such as infection, toxins, or trauma which result in the unregulated digestion of cell components. In contrast, apoptosis is a naturally occurring programmed and targeted cause of cellular death.

Apoptosis often provides beneficial effects to the organism, necrosis is almost always damaging to the surrounding tissue. Furthermore, necrotic cell death does not follow the apoptotic signal transduction pathway, but rather various receptors are activated, and result in the loss of cell membrane integrity and an uncontrolled release of products of cell death into the extracellular space.

This initiates an inflammatory response in the surrounding tissue, which attracts leukocytes and nearby phagocytes which eliminate the dead cells by phagocytosis. However, pathogen damaging substances released by leukocytes create collateral damage to surrounding tissues. This excess collateral damage inhibits the healing process. Thus, untreated necrosis results in a build-up of decomposing dead tissue and cell debris at or near the site of the cell death. A classic example of necrosis is gangrene. For this reason, it is often necessary to remove necrotic tissue surgically, a procedure known as debridement.

Thus, the ability to treat haematological cancers with DHODH inhibitor that causes apoptotic cell death is likely to lead to less side effects and an overall better therapeutic outcome.

DETAILED DISCLOSURE

DHODH is a key enzyme in the production of uridine, which is a central building block in the cell. Whilst not wishing to be bound by theory it may be that the DHODH inhibitor is able to upregulate p53 based apoptosis. The up-regulation of p53 (which may lead to cell cycle arrest and at higher levels of p 53, to apoptosis) is likely to occur via mechanisms sensing the levels of intracellular uridine, and then setting forth a series of reactions leading to stabilisation of p53, and increasing its concentration.

Unless the context indicated otherwise, the definitions of the disorders below are based on the common usage of the terms by those skilled in the art. The definitions provided below are not mutually exclusive and some specific conditions fall within more than one category.

Haematological cancer as employed herein refers to cancer of the blood, such as leukaemia, for example acute myeloid leukaemia (AML), lymphoma and myeloma. Haematological cancer as employed herein also includes plasma cell neoplasms.

Leukaemia

Leukaemia or leukemia as employed herein refers to a group of cancers that often start in the bone marrow and cause abnormally high levels of leucocytes (also known as white blood cells).

The four main types are acute lymphoblastic leukaemia (ALL), acute myeloid leukaemia (AML), chronic lymphocytic leukaemia (CLL), and chronic myeloid leukaemia (CML).

Leukaemia can also be divided into:
lymphocytic leukaemias, where the cancer is located in cells that mature into lymphocytes (white blood cells), and
myelogenous leukaemias, where the cancer is located in cells that mature into erythrocytes (red blood cells).

More specifically leukaemia includes acute lymphoblastic leukaemia, chronic lymphoblastic leukaemia, acute myelogenous leukaemia (AML), chronic myelogenous leukaemia, hairy cell leukaemia, T-cell prolymphocytic leukaemia, large granular lymphocytic leukaemia, adult T-cell leukaemia and clonal eosinophilias.

Myeloma

Myeloma as employed herein includes multiple myeloma and solitary myeloma. Multiple myeloma, is a cancer of plasma cells which causes them to form a tumor. It is often found in multiple locations in the body, hence the name multiple myeloma. When the cancer is focused in only one location it is known as solitary myeloma. In one embodiment myeloma is multiple myeloma.

In common usage the term myeloma is used to refer to multiple myeloma.

Myeloma has much in common with myeloid leukaemia. However, different cells are involved. As mentioned above myeloma involves plasma cells, whereas myeloid leukaemia involves myeloid cells. However, both cancers start in the bone marrow.

Some patients with myeloma also go on to develop acute myeloid leukaemia.

Lymphoma

Lymphoma as employed herein refers to cancerous lymphocytes. The main types of lymphoma are Hodgkin's lymphoma and non-Hodgkin lymphoma. However The World Health Organism include myelomas and immunoproliferative diseases into the generic class of lymphoma.

Subtypes of lymphomas include Hodgkin's lymphoma, non-Hodgkin's lymphoma, mature B cell neoplasms, mature T-cell neoplasms, mature NK cell neoplasms, and immunodeficiency-associated lymphoproliferative disorders.

Chronic Myeloproliferative Disorders

Chronic myeloproliferative disorders as employed herein refers to a cancer where the bone marrow makes too many abnormal red blood cells, white blood cells or platelets, which accumulate in the blood. The type of myeloproliferative disorder is based on whether too many red blood cells, white blood cells, or platelets are being made. Sometimes the body will make too many of more than one type of blood cell, but usually one type of blood cell is affected more than the others.

There are at least 6 types of chronic myeloproliferative disorders: chronic myelogenous leukaemia (CML), polycythemia vera, primary myelofibrosis (also called chronic idiopathic myelofibrosis), essential thrombocythemia, chronic neutrophilic leukaemia, and chronic eosinophilic leukaemia. Chronic myeloproliferative disorders sometimes become acute leukaemia, in which too many abnormal white blood cells are made.

Myelodysplastic Syndrome

Myelodysplastic syndrome (MDS) is a group of cancers in which immature blood cells in the bone marrow do not mature. The syndrome includes chronic myelomonocytic leukaemia (CMML), refractory anaemia with excess blasts, and refractory anaemia with ring sideroblasts. MDS can be further classified into various subtypes, including:

Myelodysplastic syndrome with ring sideroblasts. This subtype has a low number of one or more blood cell types, i.e. white blood cells, red blood cells or platelets. A characteristic feature is that existing red blood cells in the bone marrow contain a ring of excess iron called ring sideroblasts.

Myelodysplastic syndrome with unilineage dysplasia. In this subtype, one of the blood cell type is low in number and appears abnormal under a microscope.

Myelodysplastic syndrome with multilineage dysplasia. In this subtype, two or three blood cell types are abnormal.

Myelodysplastic syndrome with excess blasts—types 1 and 2. In both these subtypes, any of the three types of blood cells might be low and appear abnormal under a microscope. In addition, very immature blood cells (blasts) are found in the blood and bone marrow.

Myelodysplastic syndrome associated with isolated del chromosome abnormality. In this subtype, patients have low numbers of red blood cells and the cells have a specific mutation in their DNA.

Myelodysplastic syndrome, unclassifiable. In this subtype, there are reduced numbers of one of the three types of mature blood cells, and either the white blood cells or platelets look abnormal under a microscope.

Monoclonal Gammopathy of Underdetermined Significance (MGUS)

Monoclonal gammopathy of underdetermined significance is where an abnormal protein produced by plasma cells, known as monoclonal protein or M protein, is present in the blood. The condition is benign but in some patients is a pre-cursor to a haematological cancer.

Plasmacytoma

Plasmacytoma is a plasma cell neoplasm which forms tumors when the plasma cells become cancerous and grow out of control.

Plasmacytomas crowd out normal cells in the bone marrow as well as invade the hard outer part of the bone and then spread into the cavities of the large bones in the body. Plasmacytoma in the bones may cause pain or broken bones. Plasmacytoma of the bone often becomes multiple myeloma. When only one tumor is formed, it is called a solitary plasmacytoma. When multiple small tumors are formed, the disease is multiple myeloma. Plasmacytomas can also invade soft tissue in the body. Plastacytoma in soft tissue can press on nearby areas and cause pain such as the throat, tonsils or sinuses.

Amyloidosis

Amyloidosis is a group of diseases. However, in the present specification Amyloidosis will generally refer to AL amyloidosis (previously known as "primary systemic amyloidosis") generally in the context of the hematological cancer. AL can exist in the absence of a hematological cancer but in one embodiment the present disclosure it not concerned with this aspect.

In AL amyloidosis, the amyloid forming protein is derived from the light chain component of an immunoglobulin. These light chains are produced by abnormal plasma cells or B cells, which are usually in the bone marrow.

The underlying bone marrow disorder that causes the abnormal cells is, for example monoclonal gammopathy of undetermined significance, and in most cases is very subtle.

In some instances the underlying bone marrow disorder is multiple myeloma.

A patient with myeloma may have or develop AL amyloidosis, but it is rare for a patient with AL amyloidosis (who does not have myeloma at presentation) to progress to full blown myeloma.

AL amyloidosis can be due to abnormal light chains produced by lymphomas or chronic lymphocytic leukaemia (CLL).

Employing a combination therapy, for example where the second therapy is an inhibitor of the DNA repair and/or a pan-HER inhibitor may be particular beneficial to minimises the cancers ability to resist treatment, in particular by "attacking" the cancer cells by two or more mechanisms with the combination therapy.

In one embodiment the DHODH inhibitor of the present disclosure is employed in a combination therapy comprising chemotherapy, in particular a chemotherapy described herein.

Thus, there is provided a method of treating a patient comprising administering a therapeutically effective amount of an inhibitor of at least HER2 and a therapeutically effective amount of DHODH inhibitor.

In one embodiment the pan-HER inhibitor is an inhibitor of at least two HER receptors. In one embodiment at least one of the HER receptors inhibited is HER2.

In one embodiment the pan-HER inhibitor is an organic chemistry molecule, for example with a molecular weight of 500 or less.

In one embodiment the pan-HER inhibitor has a molecular formula of formula (I) (disclosed in WO2005/016346 fully incorporated herein by reference).

In one embodiment the pan-HER inhibitor is an inhibitor of one or more HER receptors independently selected from HER1, HER2, HER3, and HER4.

In one embodiment the biological therapeutic agent is administered parenterally.

In one embodiment the pan-HER inhibitor is a compound of formula (Ia):

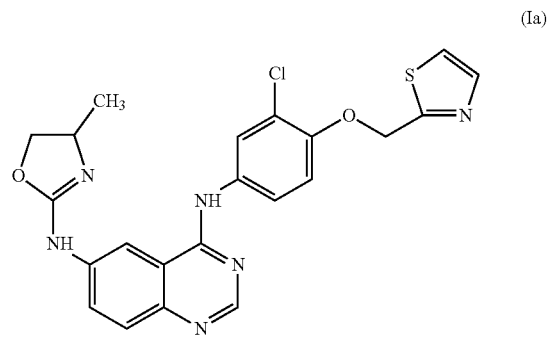 [SMILES: CC1COC(Nc2ccc3ncnc(Nc4ccc(OCc5nccs5)c(Cl)c4)c3c2)=N1]

an enantiomer thereof or a pharmaceutically acceptable salt of any one of the same.

In one embodiment the pan-HER inhibitor is Varlitinib:

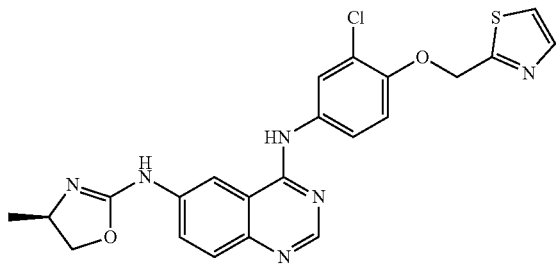 [SMILES: C[C@@H]1COC(Nc2ccc3ncnc(Nc4ccc(OCc5nccs5)c(Cl)c4)c3c2)=N1]

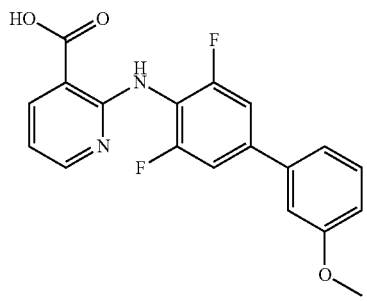 [SMILES: COc1cccc(-c2cc(F)c(Nc3ncccc3C(=O)O)c(F)c2)c1]

or a pharmaceutically acceptable salt thereof.

In one embodiment Varlitinib is employed as a free base.

Varlitinib at an appropriate dose is capable of inhibiting HER1, HER2 and HER4 directly and thought to be capable of inhibiting HER3 indirectly.

In one embodiment the compound of formula (I) (including formula (Ia) and Varlitinib) at least inhibits the activity of HER1 and HER2, HER1 and HER4 or HER2 and HER4.

In one embodiment the compound of formula (I) (including formula (Ia) and Varlitinib) at least inhibits the activity of HER1, HER2 and HER4, for example directly inhibits the activity of HER1, HER2 and HER4.

In one embodiment the compound of formula (I) (including formula (Ia) and Varlitinib) inhibits the activity of HER1, HER2, HER3 and HER4, for example directly inhibits the activity of HER1, HER2, and HER4, and indirectly inhibits the activity of HER3

In one embodiment each dose of the compound of formula (I), (including formula (Ia) and Varlitinib) is in the range 100 to 900 mg, for example each dose is in the range of 300 to 500 mg, such as 400 mg, for example administered once or twice daily, such as twice daily.

In some instances patients may benefit from having the initial dose reduced to 300 mg or 200 mg bi-daily.

Other patients may benefit from receiving the compound of formula (I), such as Varlitinib in a regime which is non-continuous, for example taking medication on alternate days instead of each day or taking medication for four sequential days followed by one, two or three days without medication.

In one embodiment the compound of formula (I), (including formula (Ia) and Varlitinib) is administered orally.

In one embodiment the HER inhibitor is a combination of HER inhibitors, for example a combination of Varlitinib and Herceptin (trastuzumab) and/or pertuzumab.

Surprisingly a combination of Varlitinib and Herceptin show more therapeutic activity than either entity alone.

In one embodiment the HER inhibitor is a combination of ado-trastuzuma-emtansine and Varlitinib.

In one embodiment, the DHODH inhibitor is 2-(3, 5-difluoro-3'-methoxybiphenyl-4-ylamino) nicotinic acid (referred to herein as ASLAN003) or a pharmaceutically acceptable salt thereof, in particular:

In one embodiment the DHODH inhibitor is administered daily, for example once daily.

References to a DHODH inhibitor or salt thereof as employed herein includes providing the compound as a prodrug, such as an ester that is converted to the active ingredient in vivo.

In one embodiment the DHODH inhibitor is administered orally.

In one embodiment the DHODH inhibitor and the second therapy, such as a pan-HER inhibitor (such as particular Varlitinib) are administered sequentially in a treatment regimen, for example are administered on the same day.

In one embodiment the pan-HER inhibitor such as Varlitinib is administered twice daily, for example a dose in the range disclosed herein.

In one embodiment the DHODH inhibitor and the second therapy, such as a HER inhibitor (such as HER2 or pan HER inhibitor) are administered simultaneously, at approximately the same time.

In one embodiment the DHODH inhibitor is administered in regimen that is daily or weekly for a continuous period of time for example 1 to 60 months or more, and the second therapy, such as a HER2 inhibitor or pan-HER inhibitor is administered intermittently during this period, for example Varlitinib may be administered in a one or more 28 days cycles. Where the pan-HER inhibitor comprises an antibody molecule, such as Herceptin then the administration protocol is likely to be very different to that of small molecule inhibitors. Herceptin, for example may be administered (in particular in combination with cytotoxic chemotherapy) in a regime as follows:
1) First administration 4 mg/Kg over 90 minute;
2) Weekly administrations of 2 mg/Kg over 30 minutes for the next 12 weeks; and
3) One week post 2) initiation of 6 mg/Kg over 30-90 minutes every three weeks.

In one embodiment the second therapy, such as the pan-HER inhibitor is administered in regimen that is daily or weekly for a continuous period of time, for example 1 to 60 months or more, and the DHODH inhibitor is administered intermittently during this period.

Administered intermittently as employed herein refers to a period wherein the therapy is administered and then stopped with the option of starting the therapy again at some point in the future or simply stopped for a specific period of time and then restarted in accordance with a treatment plan.

In one embodiment the DHODH inhibitor is administered in regimen that is daily or weekly for a continuous period of time, for example 1 to 60 months or more, and the second therapy, such as a pan-HER inhibitor is administered in regimen that is daily or weekly for a continuous period of time, for example 1 to 60 months or more.

In one embodiment the DHODH inhibitor is administered in regimen that is daily or weekly for intermittent periods over for example 1 to 60 months or more, and the pan-HER inhibitor is administered conjunctly with DHODH inhibitor in regimen that is daily or weekly for intermittent periods over, for example 1 to 60 months or more.

In one embodiment the DHODH inhibitor and the pan-HER inhibitor are co-formulated.

In one embodiment the DHODH inhibitor is administered orally.

In one embodiment the second therapy, such as a HER inhibitor is administered orally, parenterally or both, in particular orally.

In one embodiment the second therapy, for example a HER inhibitor, such as HER2 inhibitor is administered orally or parenterally, for example intravenously.

In one embodiment the second therapy, for example a HER inhibitor, such as pan-HER inhibitor is administered orally.

In one embodiment employing a combination of HER inhibitors one is administered orally and one is administered parenterally, such as intravenously.

In one embodiment the DHODH inhibitor and the second therapy, for example the pan-HER inhibitor are both administered orally.

In one embodiment the patient is a human.

The benefits of employing the DHODH inhibitor ASLAN003, even as a monotherapy, include the fact that the cancer cells are killed by apoptosis as opposed to via a necrotic mechanism. This is surprising because DHODH inhibitors such as leflunomide and teriflunomide kill cancer cells via a necrotic mechanism.

In one embodiment the combination therapy of the present disclosure is efficacious and, for example beneficial in that it provides augmented therapeutic activity in comparison to monotherapy comprising one of the components.

Augmented activity may be any beneficial therapeutic effect of employing the combination of the present disclosure, for example an increase in anti-tumor activity and/or a reduced propensity for the cancer to become resistant. Other benefits may be therapeutic effect in patients who have failed one or more lines of therapy. Thus in one embodiment the patient population has a cancer that is resistant or refractory to known therapies, such as cytotoxic chemotherapy.

Unless the context indicated otherwise refractory and resistant are used to interchangeably herein to refer to where the cancer does not respond to therapy or does not responds poorly to therapy.

Combination therapy as employed herein refers to two or more modes of therapy being employing over the same treatment period, i.e. the opposite of sequential therapy. Thus, combination therapy refers to where a medicament according to the present disclosure is administered in a treatment regimen along with at least one further therapeutic agent. The regime may be separate formulations administered at the same time or different times or co-formulations of the two or more therapeutic agents. The "first" medicament employed in the combination therapy according to the present disclosure may be administered; prior to the further therapeutic agent or agents of the disclosure, concomitant with the further therapeutic agent or agents of the disclosure, or after the further therapeutic agent or agents of the disclosure.

Two or more modes of therapy as employed herein refers to at least two therapies which have different modes of action and/or different activities and/or different routes of administration.

To obtain the benefits of the combination therapy of the present disclosure the "second" therapy, for example the HER inhibitor and the DHODH inhibitor have to be administered in a time frame, where the pharmacological effects of a both therapies overlap, i.e. the treatment regimens for the said therapies partly coincide in time. A skilled person will understand in practice what this means.

In one embodiment further therapeutic agent or agents, such as an anti-cancer therapy (in particular chemotherapy) are employed in combination with the monotherapy or combination therapy of the present disclosure.

In one embodiment the therapeutic agent is a chemotherapeutic agent. Chemotherapeutic agent as employed herein is intended to refer to specific antineoplastic chemical agents or drugs that are destructive to malignant cells and tissues, including alkylating agents, antimetabolites, anthracyclines, plant alkaloids, topoisomerase inhibitors, and other antitumour agents. Specific examples of chemotherapy include doxorubicin, 5-fluorouracil (5-FU), paclitaxel (for example abraxane or docetaxel), capecitabine, irinotecan, and platins, such as cisplatin and oxaliplatin or a combination thereof. A suitable dose may be chosen by the practitioner based on the nature of the cancer being treated and the patient.

Co-administered as employed herein refers to administration of DHODH inhibitor and the second therapeutic agents (such as the HER inhibitor and/or chemotherapy) at the same time or approximately the same time (including where the actives are administered by the same or different routes).

Inhibitor as employed refers to a therapeutic agent that reduces a relevant biological activity, for example by 5, 10, 15, 20, 25, 30, 35, 40, 45, 50, 55, 60, 65, 70, 75, 80, 85, 90, 95 or 100%, such as when measured in a relevant in vitro assay.

Direct inhibition is where the inhibitor binds directly to or physically blocks a binding interaction to inhibit a biological activity, or when the inhibitor inhibits the activation through phosphorylation of the target molecule.

Indirect inhibition as employed herein refers to where the biological activity in question is inhibited as a result of directly inhibiting a target that is other than the entity that is indirectly inhibited.

Dihydroorotate dehydrogenase (DHODH) is the enzyme that catalyzes the fourth step in the pyrimidine biosynthetic pathway namely the conversion of dihydroorotate to orotate concomitantly with an electron transfer to ubiquinone (co-factor Q) via a flavin mononucleotide intermediate (Loffler Mol Cell Biochem, 1997). In contrast to parasites (*Plasmodium falciparum*) (McRobert et al Mol Biochem Parasitol 2002) and bacteria (*E. coli*) which exclusively have this de novo pathway as the source of pyrimidines, mammal cells have an additional salvage pathway.

During homeostatic proliferation the salvage pathway, which is independent of DHODH, seems sufficient for the cellular supply with pyrimidine bases. However, in cells with a high turnover and particularly T and B lymphocytes the de novo pathway is required to proliferate. In these cells, DHODH inhibition stops the cell cycle progression by suppressing DNA synthesis and ultimately cell proliferation (Breedveld F. C. Ann Rheum Dis 2000).

There are some suggestions that inhibition of mitochondrial cytochrome bc1, a component of the electron transport chain complex III, leads to activation of tumor suppressor p53, followed by apoptosis induction. The mitochondrial respiratory chain is coupled to the de novo pyrimidine biosynthesis pathway via the mitochondrial enzyme dihydroorotate dehydrogenase (DHODH).

The p53 activation has been shown to be triggered by the impairment of the de novo pyrimidine 15 biosynthesis due to the suppression of DHODH.

A DHODH as employed herein refers to a compound which inhibits the activity of dihydroorotate dehydrogenase, in particular in vivo. 2-(3, 5-difluoro-3'-methoxybiphenyl-4-ylamino) nicotinic acid is disclosed in WO2008/077639, incorporated herein by reference.

Pan-HER inhibitor as employed herein refers to a molecule that inhibits at least two molecules from the ErbB family of proteins, namely ErbB-1 (also known as HER1 and EGFR), ErbB-2 (HER2), ErbB-3 (HER3), and ErbB-4 (HER4). Thus pan-HER inhibitor as employed herein refers to a therapeutic agent, for example a chemical entity, which inhibits at least two HER receptors, for example an inhibitor of HER 1 and HER2.

A biological therapeutic is one based on a protein (including a polypeptide or peptide), for example an antibody or binding fragment thereof, including fusion proteins and biological molecules conjugated to a polymer, toxin or similar payload.

A "drug" as employed herein refers to a chemical entity, organic chemistry molecule with pharmacological activity.

An example of a biological therapeutic conjugated to a payload, suitable for use in the therapy of the present disclosure, is ado-trastuzumab emtansine.

In one embodiment the HER inhibitor is a HER dimerization inhibitor, for example pertuzumab disclosed in WO01/00244 and WO01/100245 incorporated herein by reference. In one embodiment the pan-HER inhibitor is a compound of formula (I) or (Ia) described above and disclosed in WO2005/016346 incorporated herein by reference, in particular (R)—N4-[3-Chloro-4-(thiazol-2-ylmethoxy)-phenyl]-N6-(4-methyl-4,5-dihydro-oxazol-2-yl)-quinazoline3,4,6-diamine (Varlitinib) or a pharmaceutically acceptable salt thereof.

Examples of pharmaceutically acceptable salts include but are not limited to acid addition salts of strong mineral acids such as HCl and HBr salts and addition salts of strong organic acids, such as a methansulfonic acid salt, tosylates furoates and the like, including di, tri salts thereof, such as ditosylates.

In one embodiment the combination therapy according to the present disclosure further comprises a RON inhibitor, for example as disclosed WO2008/058229, incorporated herein by reference.

In one embodiment the combination therapy of the present disclosure comprises a checkpoint inhibitor, such as a CTLA4 inhibitor, a PD-1 inhibitor or a PD-L1 inhibitor, in particular an antibody or binding fragment thereof.

In one embodiment the combination therapy the monotherapy or combination therapy of the present disclosure further comprises a chemotherapeutic agent.

Chemotherapeutic Agents

The therapy (such as the combination therapy) of the present disclosure may be employed in combination with a further cancer therapy, for example chemotherapy.

Chemotherapeutic agent and chemotherapy or cytotoxic agent are employed interchangeably herein unless the context indicates otherwise.

Chemotherapy as employed herein is intended to refer to specific antineoplastic chemical agents or drugs that are "selectively" destructive to malignant cells and tissues, for example alkylating agents, antimetabolites including thymidylate synthase inhibitors, anthracyclines, anti-microtubule agents including plant alkaloids, topoisomerase inhibitors, PARP inhibitors and other antitumour agents. Selectively in this context is used loosely because of course many of these agents have serious side effects.

The preferred dose may be chosen by the practitioner, based on the nature of the cancer being treated.

Examples of alkylating agents, which may be employed in the method of the present disclosure include an alkylating agent nitrogen mustards, nitrosoureas, tetrazines, aziridines, platins and derivatives, and non-classical alkylating agents.

Examples of a platinum containing chemotherapeutic agent (also referred to as platins), such as cisplatin, carboplatin, oxaliplatin, satraplatin, picoplatin, nedaplatin, triplatin and lipoplatin (a 25 liposomal version of cisplatin), in particular cisplatin, carboplatin and oxaliplatin.

The dose for cisplatin ranges from about 20 to about 270 mg/m$^2$ depending on the exact cancer. Often the dose is in the range about 70 to about 100 mg/m$^2$.

Nitrogen mustards include mechlorethamine, cyclophosphamide, melphalan, chlorambucil, ifosfamide and busulfan.

Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide.

Aziridines include thiotepa, mytomycin and diaziquone (AZQ).

Examples of antimetabolites, which may be employed in the method of the present disclosure, include anti-folates (for example methotrexate and pemetrexed), purine analogues (for example thiopurines, such as azathiopurine, mercaptopurine, thiopurine, fludarabine (including the phosphate form), pentostatin and cladribine), pyrimidine analogues (for example fluoropyrimidines, such as 5-fluorouracil and prodrugs thereof such as capecitabine [Xeloda®]), floxuridine, gemcitabine, cytarabine, decitabine, raltitrexed (tomudex) hydrochloride, cladribine 40 and 6-azauracil.

Examples of anthracyclines, which may be employed in the therapy of the present disclosure, include daunorubicin (Daunomycin), daunorubicin (liposomal), doxorubicin (Adriamycin), doxorubicin (liposomal), epirubicin, idarubicin, valrubicin currently used only to treat bladder cancer and mitoxantrone an anthracycline analog, in particular doxorubicin.

Examples of anti-microtubule agents, which may be employed in the therapy of the present disclosure, include a vinca alkaloid and/or a taxanes.

Vinca alkaloids include completely natural chemicals for example vincristine and vinblastine and also semi-synthetic vinca alkaloids, for example vinorelbine, vindesine, and vinflunine Taxanes include paclitaxel, docetaxel, abraxane, carbazitaxel and derivatives of thereof. Derivatives of taxanes as employed herein includes reformulations of taxanes like taxol, for example in a micelluar formulations, derivatives also include chemical derivatives wherein synthetic chemistry is employed to modify a starting material which is a taxane.

Topoisomerase inhibitors, which may be employed in a method of the present disclosure include type I topoisomerase inhibitors, type II topoisomerase inhibitors and type II topoisomerase poisons. Type I inhibitors include topotecan, irinotecan, indotecan and indimitecan. Type II inhibitors include genistein and ICRF 193 which has the following structure:

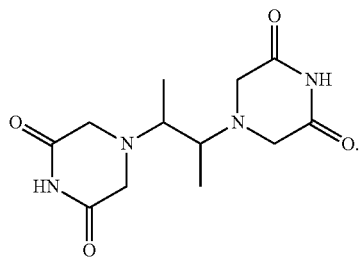 [SMILES: CC(C(C)N1CC(=O)NC(=O)C1)N1CC(=O)NC(=O)C1]

Type II poisons include amsacrine, etoposide, etoposide phosphate, teniposide and 20 doxorubicin and fluoroquinolones.

In one embodiment the chemotherapeutic is a PARP inhibitor.

In one embodiment the chemotherapy comprises 5-FU or a prodrug thereof.

In one embodiment the chemotherapy comprises capecitabine.

In one embodiment the chemotherapy comprises gemcitabine.

In one embodiment the chemotherapy comprises FOLFOX.

In one embodiment a combination of chemotherapeutic agents employed is, for example a platin and 5-FU or a prodrug thereof, for example cisplatin or oxaplatin and capecitabine or gemcitabine, such as FOLFOX.

In one embodiment the chemotherapy comprises a combination of chemotherapy agents, in particular cytotoxic chemotherapeutic agents.

In one embodiment the chemotherapy combination comprises a platin, such as cisplatin and fluorouracil or capecitabine.

In one embodiment the chemotherapy combination in capecitabine and oxaliplatin (Xelox).

In one embodiment the chemotherapy is a combination of folinic acid and 5-FU, optionally in combination with oxaliplatin.

In one embodiment the chemotherapy is a combination of folinic acid, 5-FU and irinotecan (FOLFIRI), optionally in combination with oxaliplatin (FOLFIRINOX). The regimen, for example consists of: irinotecan (180 mg/m$^2$ IV over 90 minutes) concurrently with folinic acid (400 mg/m$^2$[or 2×250 mg/m$^2$] IV over 120 minutes); followed by fluorouracil (400-500 mg/m$^2$ IV bolus) then fluorouracil (2400-3000 mg/m$^2$ intravenous infusion over 46 hours). This cycle is typically repeated every two weeks. The dosages shown above may vary from cycle to cycle.

In one embodiment the chemotherapy combination employs a microtubule inhibitor, for example vincristine sulphate, epothilone A, N-[2-[(4-Hydroxyphenyl)amino]-3-pyridinyl]-4methoxybenzenesulfonamide (ABT-751), a taxol derived chemotherapeutic agent, for example paclitaxel, abraxane, or docetaxel or a combination thereof.

In one embodiment the chemotherapy combination employs an mTor inhibitor. Examples of mTor inhibitors include: everolimus (RAD001), WYE-354, KU-0063794, papamycin (Sirolimus), Temsirolimus, Deforolimus (MK-8669), AZD8055 and BEZ235 (NVP-BEZ235).

In one embodiment the chemotherapy combination employs a MEK inhibitor. Examples of MEK inhibitors include: AS703026, CI-1040 (PD184352), AZD6244 (Selumetinib), PD318088, PD0325901, AZD8330, PD98059, U0126-EtOH, BIX 02189 or BIX 02188.

In one embodiment the chemotherapy combination employs an AKT inhibitor. Examples of AKT inhibitors include: MK-2206 and AT7867.

In one embodiment the combination employs an aurora kinase inhibitor. Examples of aurora kinase inhibitors include: Aurora A Inhibitor I, VX-680, AZD1152-HQPA (Barasertib), SNS314 Mesylate, PHA-680632, ZM-447439, CCT129202 and Hesperadin.

In one embodiment the chemotherapy combination employs a p38 inhibitor, for example as disclosed in WO2010/038086, such as N-[4-({4-[3-(3-tert-Butyl-1-p-tolyl-1H-pyrazol-5yl)ureido]naphthalen-1-yloxy}methyl)pyridin-2-yl]-2-methoxyacetamide.

In one embodiment the combination employs a Bcl-2 inhibitor. Examples of Bcl-2 inhibitors include: obatoclax mesylate, ABT-737, ABT-263 (navitoclax) and TW-37.

In one embodiment the chemotherapy combination comprises an antimetabolite such as capecitabine (xeloda), fludarabine phosphate, fludarabine (fludara), decitabine, raltitrexed (tomudex), gemcitabine hydrochloride and cladribine.

In one embodiment the chemotherapy combination comprises ganciclovir, which may assist in controlling immune responses and/or tumour vasculation.

In one embodiment the chemotherapy includes a PARP inhibitor.

In one embodiment one or more therapies employed in the method herein are metronomic, that is a continuous or frequent treatment with low doses of anticancer drugs, often given concomitant with other methods of therapy.

In one embodiment, there is provided the use of multiple cycles of treatment (such as chemotherapy) for example 2, 3, 4, 5, 6, 7, 8.

In one embodiment the therapy of the present disclosure is employed after chemotherapy.

In one embodiment the therapy of the present disclosure is employed before chemotherapy.

In one embodiment the therapy of the present disclosure is employed concomitant with a chemotherapy regime.

In one embodiment the dose of chemotherapy employed in the therapy of the present disclosure is lower than the dose of chemotherapy employed in "monotherapy" (where monotherapy may include the dose of chemotherapy employed when combinations of chemotherapy agents are employed).

In one embodiment the medicament is administered in combination with therapy complimentary to the cancer therapy, for example a treatment for cachexia, such as cancer cachexia, for example S-pindolol, S-mepindolol or S-bopindolol. Suitable doses may be in the range of 2.5 mg to 100 mg, such as 2.5 mg to 50 mg per day provided a single dose or multiple doses given as multiple doses administered during the day.

Treatment

Treatment as employed herein refers to where the patient has a disease or disorder, for example cancer and the medicament according to the present disclosure is administered to stabilise the disease, delay the disease, amelorate the disease, send the disease into remission, maintain the disease in remission or cure the disease. Treating as employed herein includes administration of a medicament according to the present disclosure for treatment or prophylaxis. The present disclosure is explained in the context of a method of treating a patient. However, the disclosure extends to use of the therapy as described herein for use in treatment, in particular for the treatment of cancer, such as a cancer described herein. Also provided is use of the compounds as described herein for the manufacture of a medicament for the treatment of cancer, in particular a cancer described herein.

In one embodiment the cancer is AML.

In one embodiment the cancer is MDS.

In one embodiment the combination therapy according to the present disclosure is employed as cancer adjuvant therapy, for example after surgery to remove some or all of the cancerous cells.

In one embodiment the therapy according to the present disclosure is employed as neoadjuvant therapy, for example before surgery to remove some or all of the cancerous cells.

In one embodiment a therapeutically effective dose (such as a daily dose) of a DHODH inhibitor is in the range 10 mg to 1000 mg, for example 50 to 500 mg, such as 50, 100, 150, 200, 250, 300, 350, 400, 450, 500 mg, in particular 200 or 300 mg administered once a day.

In one embodiment the DHODH inhibitor 2-(3, 5-difluoro-3'-methoxybiphenyl-4-ylamino) nicotinic acid or a pharmaceutically acceptable salt thereof is co-formulated with a second therapy, for example for oral administration.

In one embodiment the patient is a human, for example an adult or a child. A child as employed herein refers a person 12 years old or less.

In the context of this specification "comprising" is to be interpreted as "including".

Embodiments of the invention comprising certain features/elements are also intended to extend to alternative embodiments "consisting" or "consisting essentially" of the relevant elements/features.

Where technically appropriate, embodiments of the invention may be combined.

Technical references such as patents and applications are incorporated herein by reference.

Any embodiments specifically and explicitly recited herein may form the basis of a disclaimer either alone or in combination with one or more further embodiments. Heading herein are employed to divide the document into sections and are not intended to be used to construe the meaning of the disclosure provided herein.

The priority documents GB 1703453.9, SG 10201700518Q, SG 10201704475Y, and SG 10201706887Q are incorporated herein by reference.

EXAMPLE 1—IN VITRO ANALYSIS OF ASLAN003 AGAINST AML CELL LINES FROM DIFFERENT FAB CLASSIFICATION SUBTYPES AND THAT ARE IN DIFFERENT STAGES OF BLAST CELL DIFFERENTIATION

The AML cell lines were dosed with the varying concentrations of ASLAN003 and differentiation of the cell lines were observed via upregulation of CD11b and CD14 on the cell surface via flow cytometry. Differentiation was also determined using the NBT assay and from morphological observations from Wright-Giemsa staining.

| AML Cell Line | FAB Classification | ASLAN003 Differentiation |
|---|---|---|
| KG-1 | M0/M1 | Positive |
| MOLM-14 | M5 | Positive |
| THP-1 | M5 | Positive |
| HL-60 | M2 | Negative |
| NB-4 | M3 | Negative |

The results are shown in FIGS. 1 to 8 and summarised in the table above.

The myeloid differentiation effects of ASLAN003 were observed in KG-1, MOLM-14 and THP-1 cell lines. However, dosing of HL-60 and NB-4 AML cell lines with ASLAN003 did not induce observed differentiation effects.

EXAMPLE 2—AN IN VIVO ANALYSIS OF ASLAN003 CARRIED OUT IN MOLM-14 XENOGRAFT MODEL

Figure 1A:
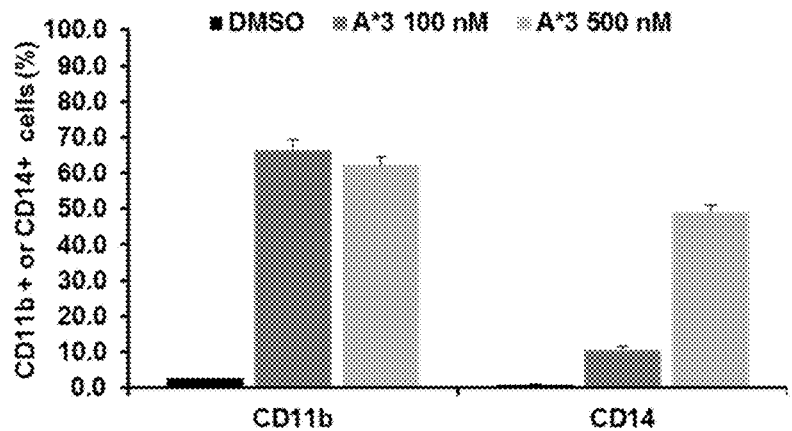
FIGS. 1A&B Shows ASLAN003 induction of CD11b and CD14 in various AML cell lines (A) MOLM-14 (M5), THP-1 (M5) and NB-4 (M3) (B) KG-1 (MO/1) and HL-60 (M2)
Figure 1A:
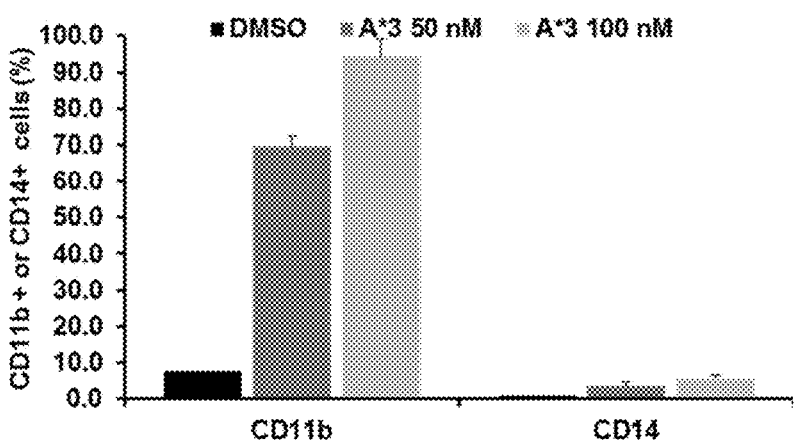
Figure 1A:
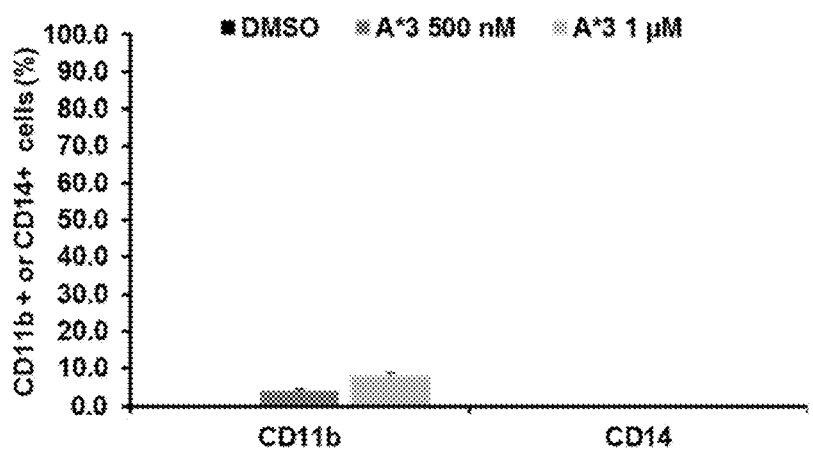
Figure 1B:
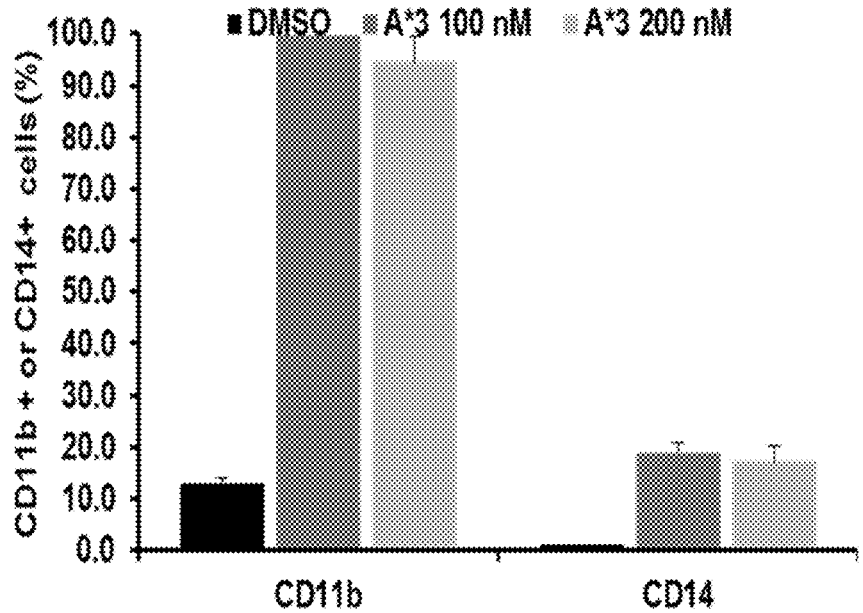
Figure 1B:
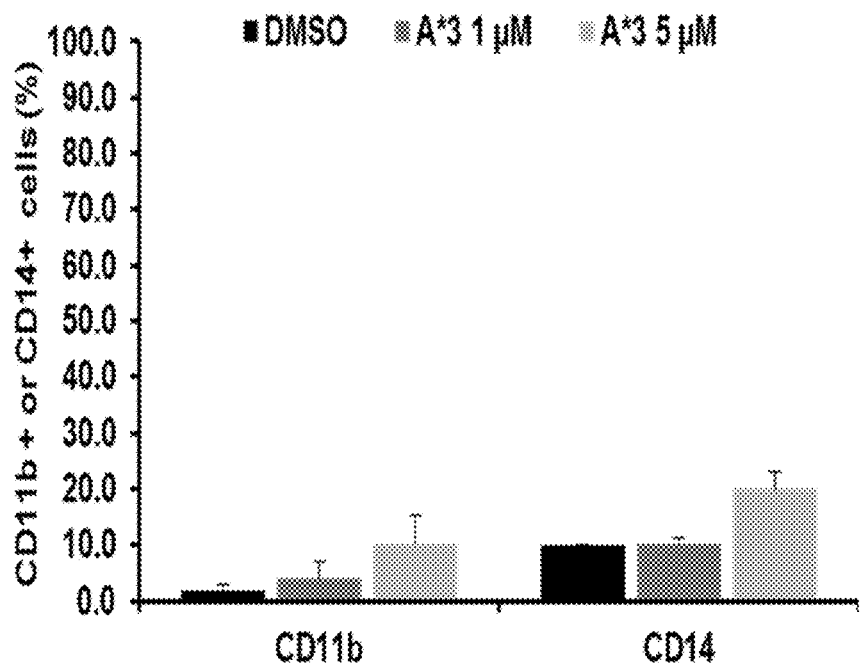
Figure 2:
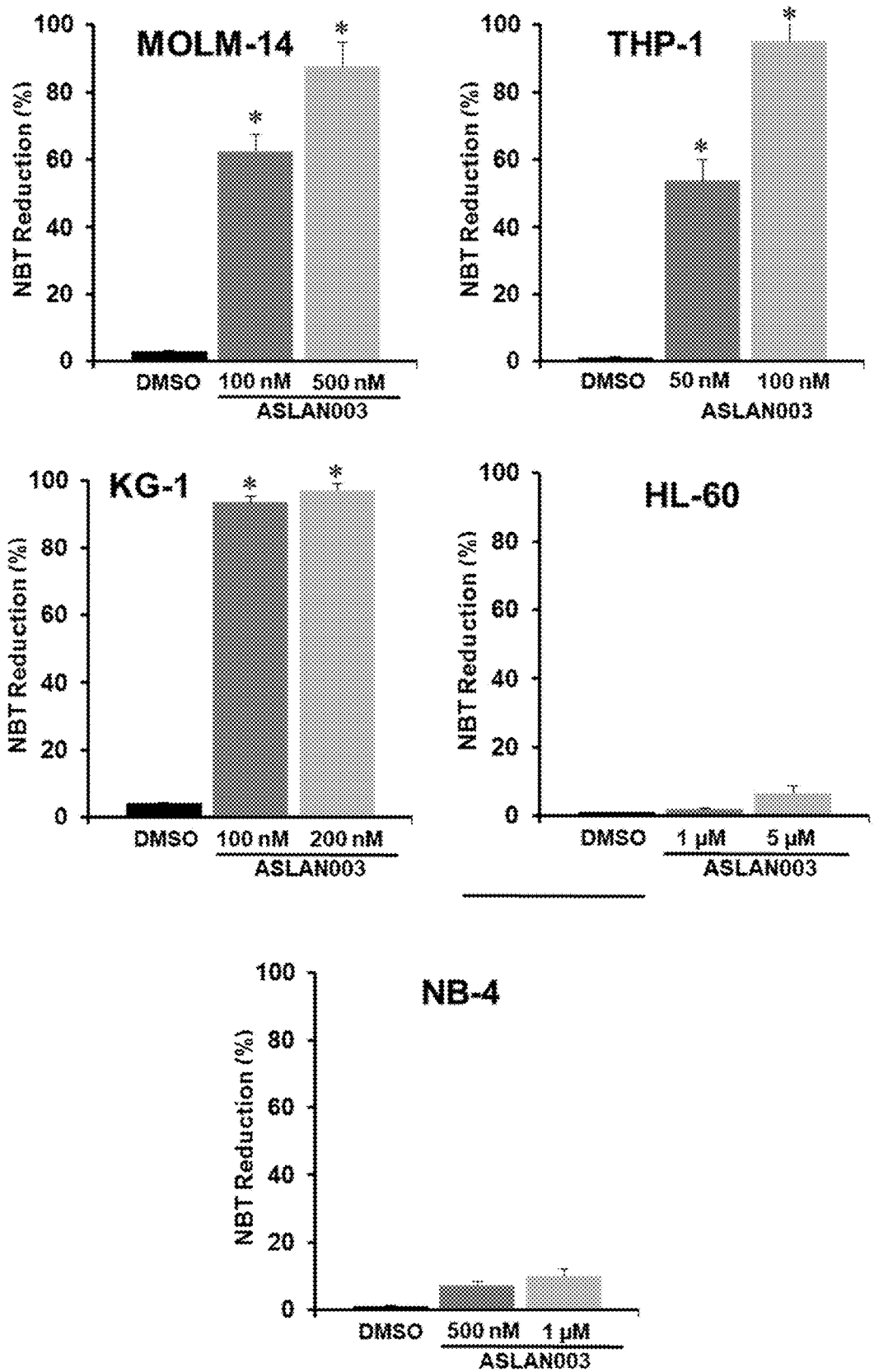
FIG. 2 Shows NBT reduction activity for ASLAN003
Figure 3:
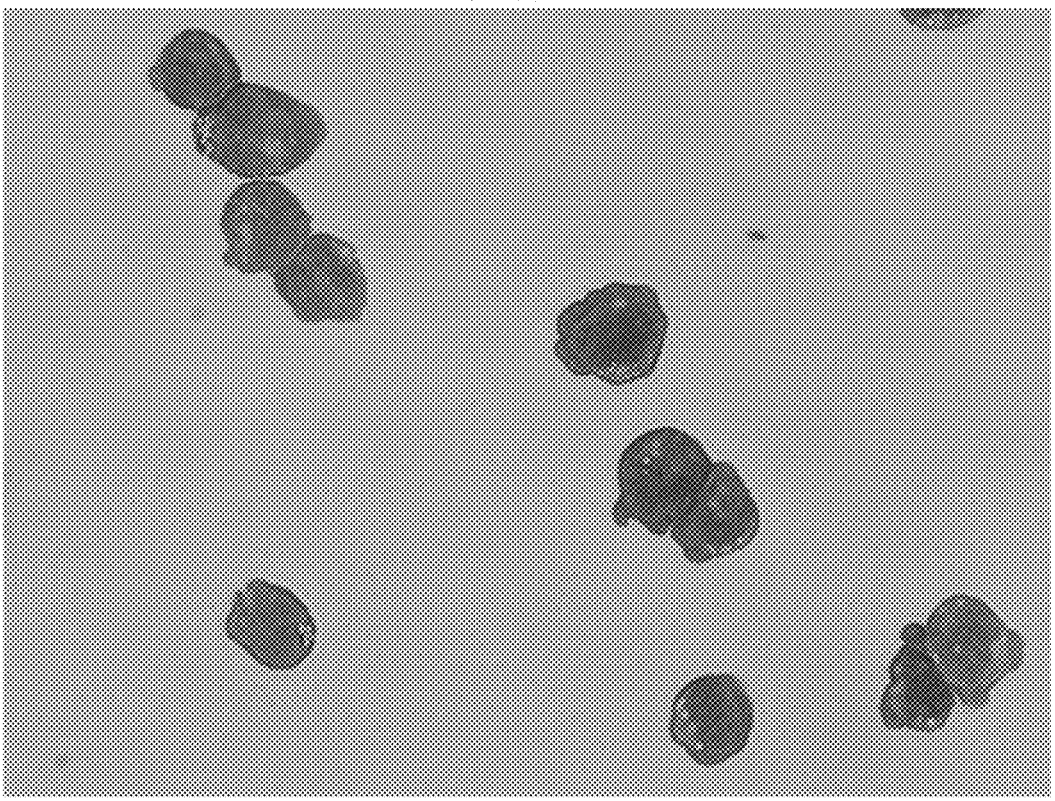
FIG. 3 Shows Giemsa Staining for MOLM-14 cells after treatment with ASLAN003 or a control for 96 hours FIG. 4 Shows NBT assay results for MOLM-14 cells after treatment for with ASLAN003 or a control for 96 hours FIG. 5 Shows Giemsa Staining for THP-1 (M5) cells after treatment with ASLAN003 or a control for 96 hours FIG. 6 Shows NBT assay results for THP-1 (M5) cells after treatment for with ASLAN003 or a control for 96 hours FIG. 7 Shows Giemsa Staining for NB-4 cells after treatment with ASLAN003 or a control for 96 hours FIG. 8 Shows NBT assay results for NB-4 cells after treatment for with ASLAN003 or a control for 96 hours FIG. 9 Shows survival of MOLM-14 xenograft mice following administration of ASLAN003. Median survival: Vehicle group 24 days, ASLAN003 group 27 days FIG. 10 Shows percentage of CD45+ cells in bone marrow, peripheral blood, spleen and liver of MOLM-14 xenograft following administration of ASLAN003
Figure 3:
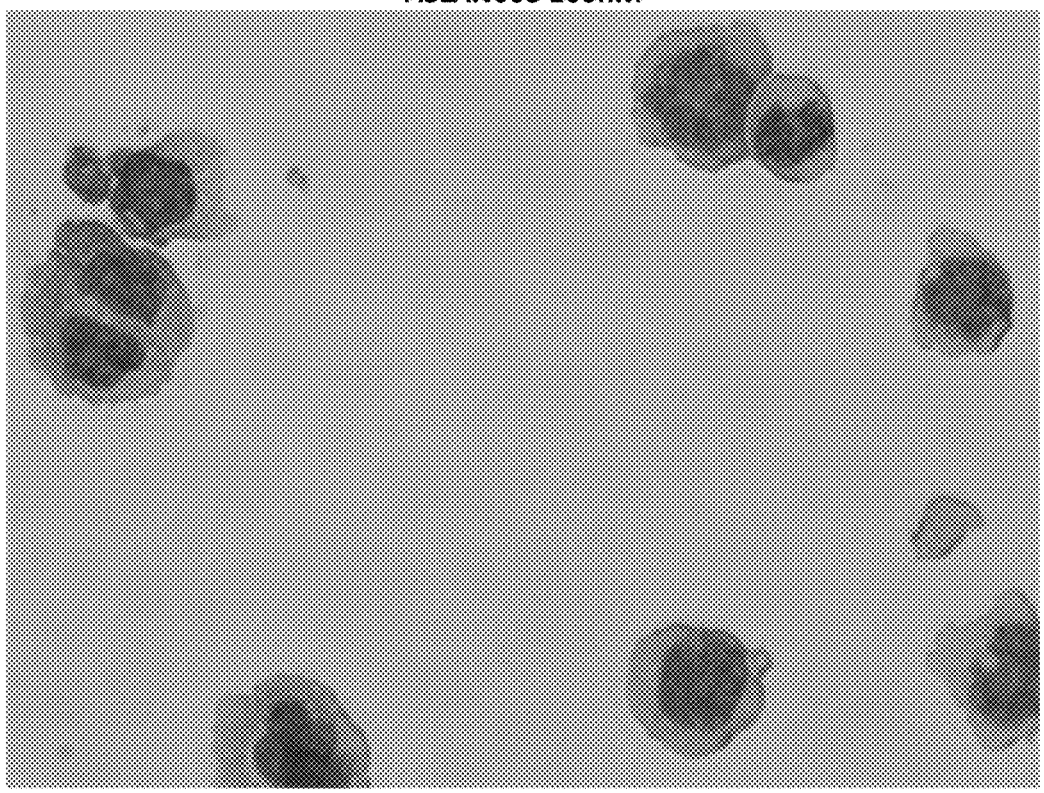
Figure 4:
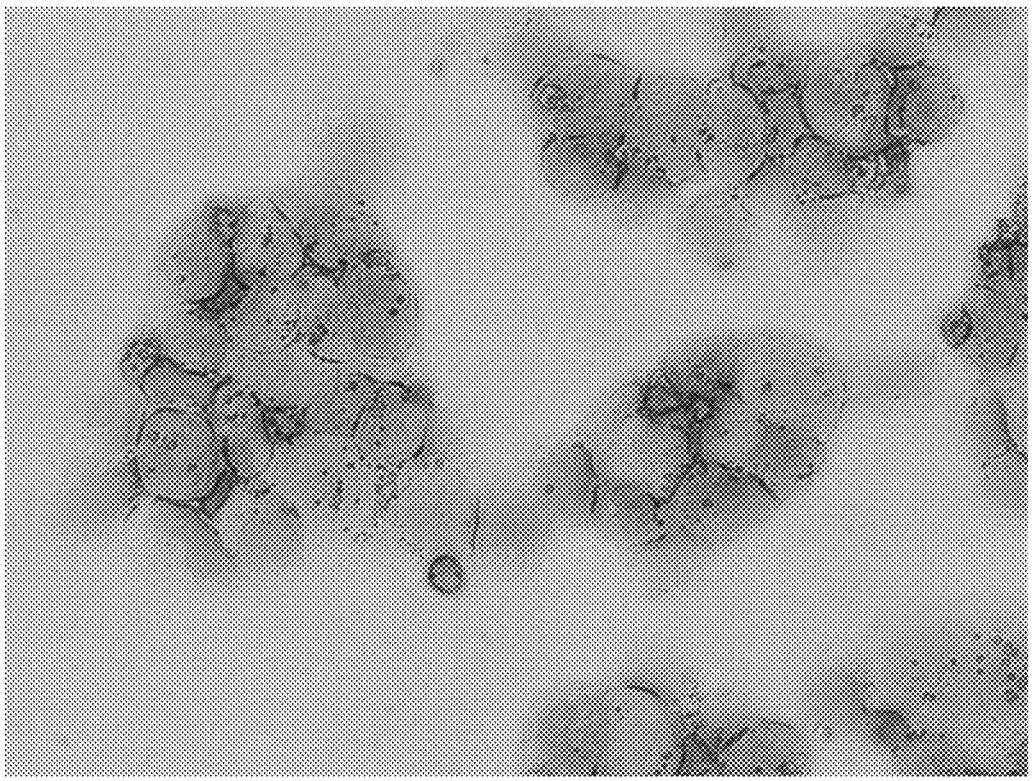
Figure 4:
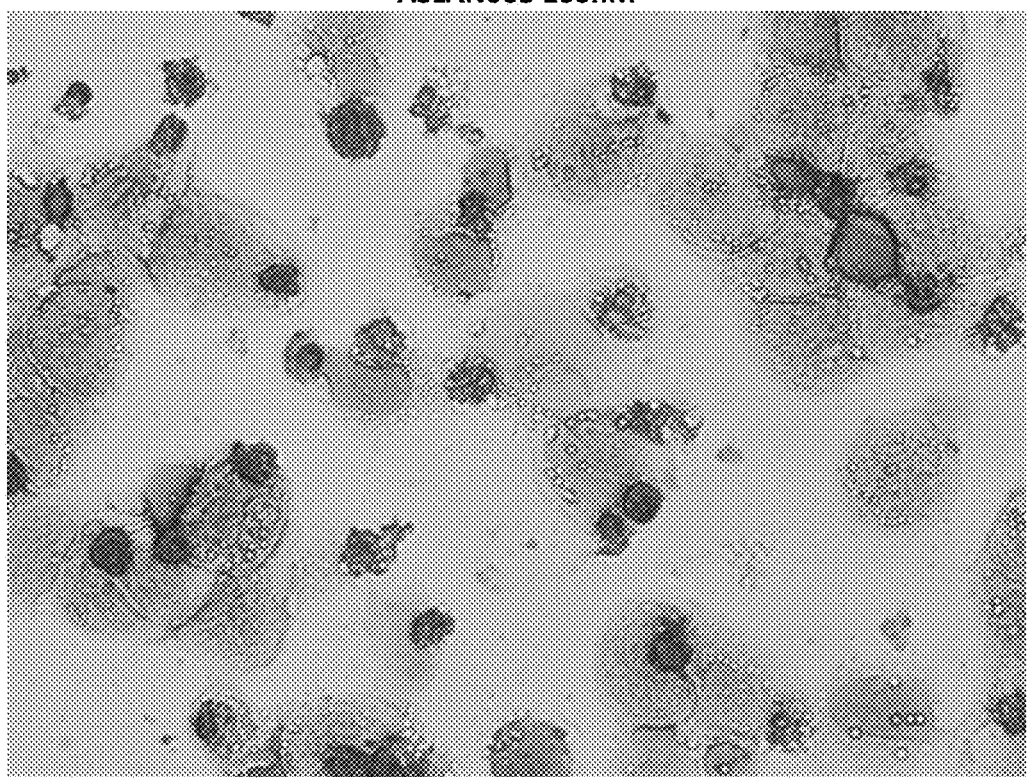
Figure 5:
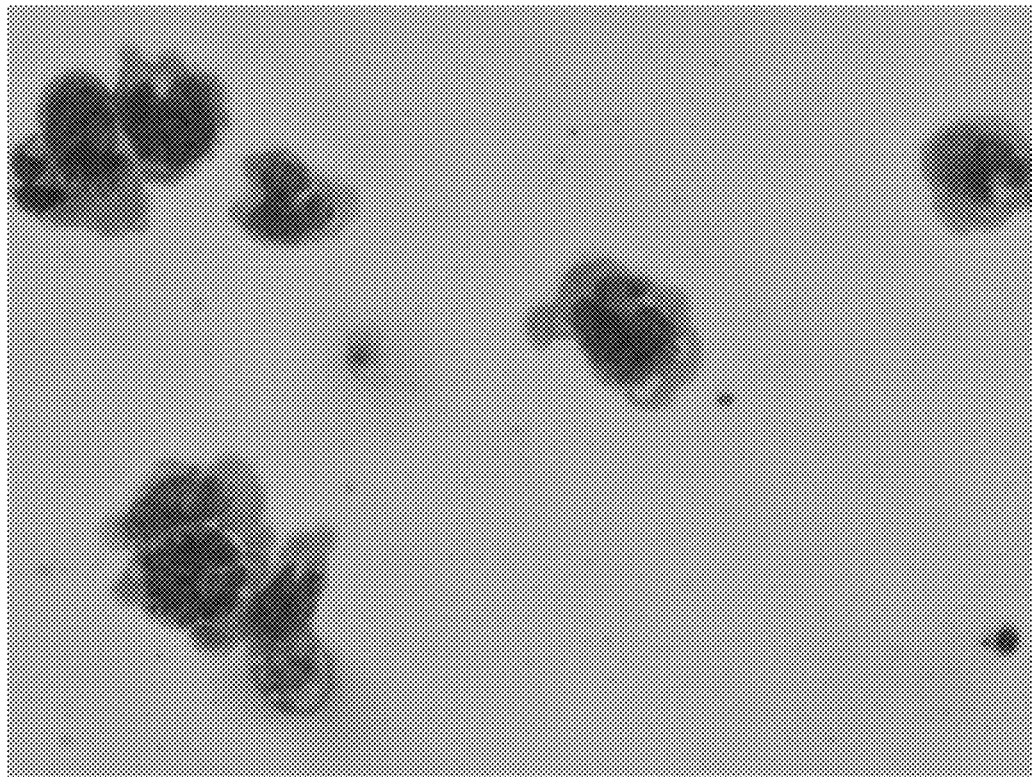
Figure 5:
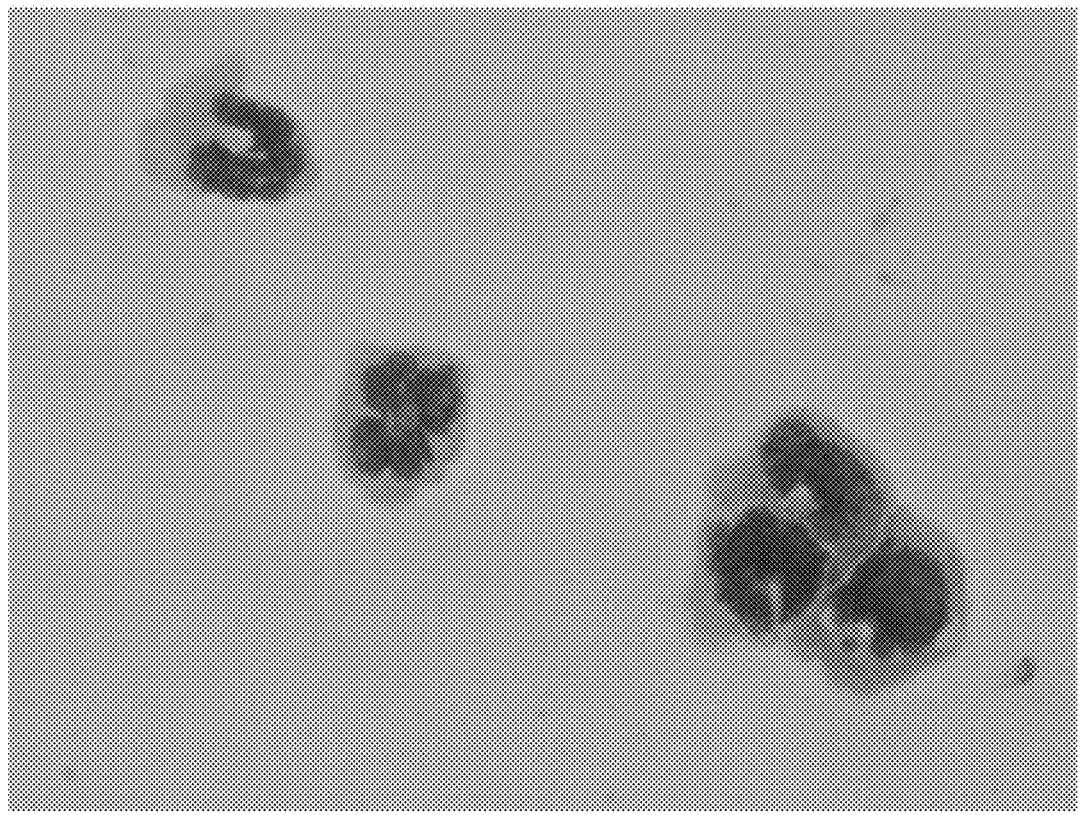
Figure 6:
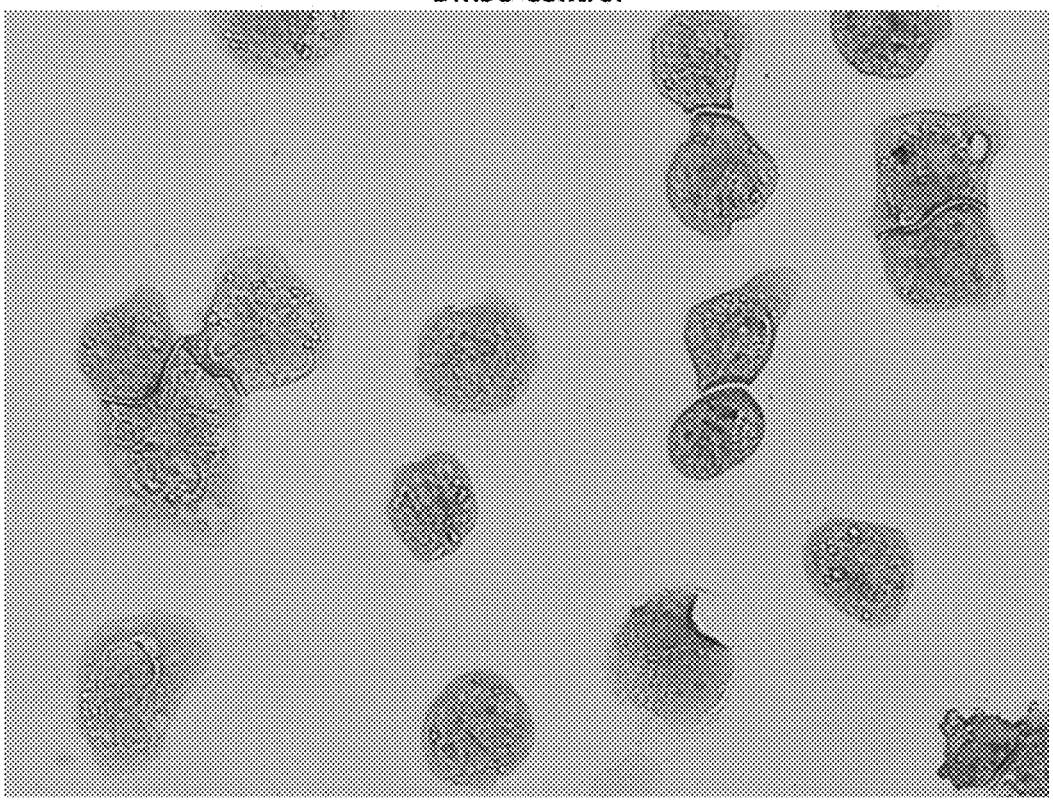
Figure 6:
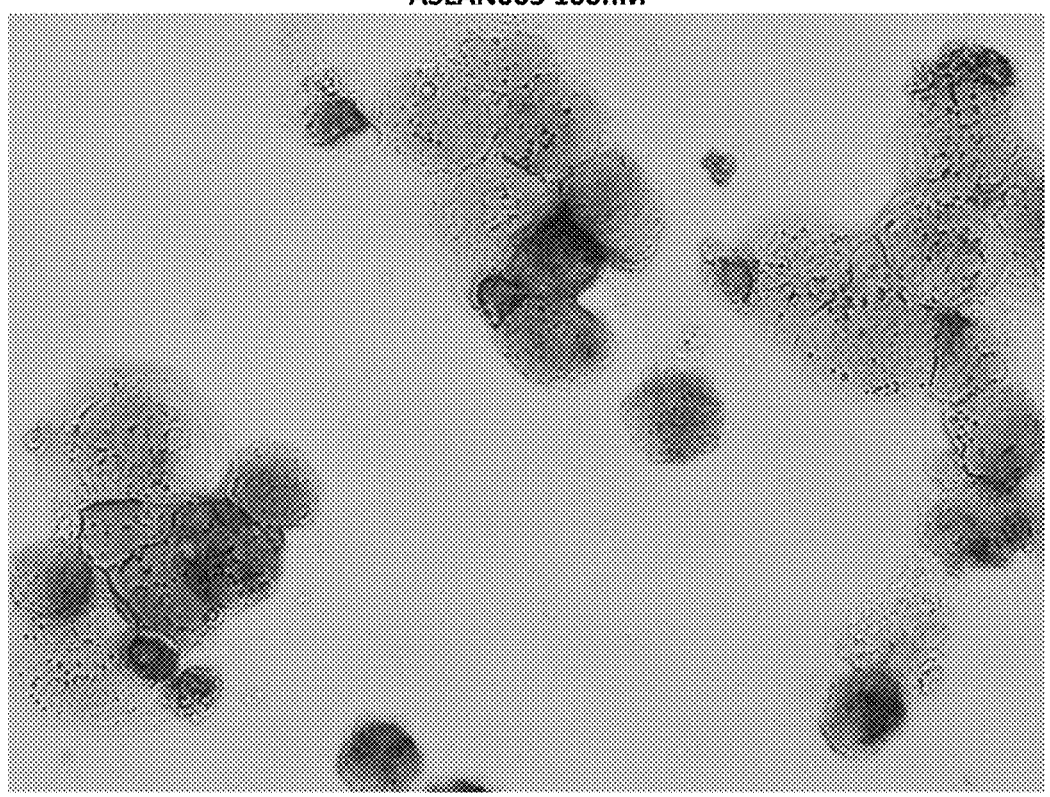
Figure 7:
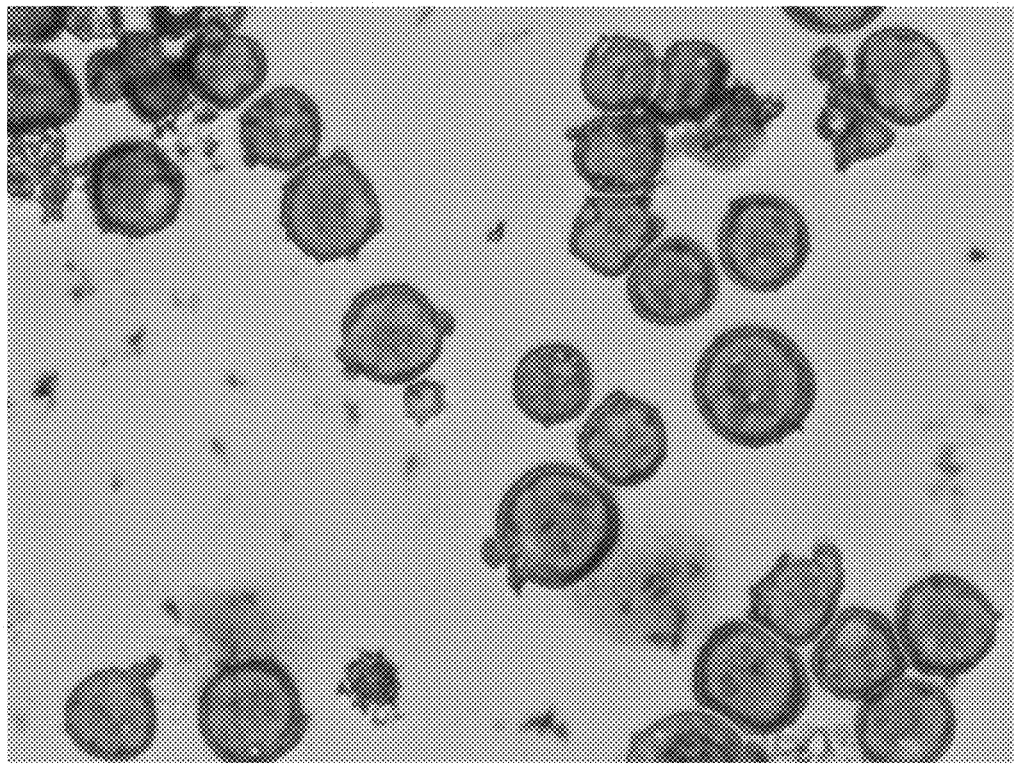
Figure 7:
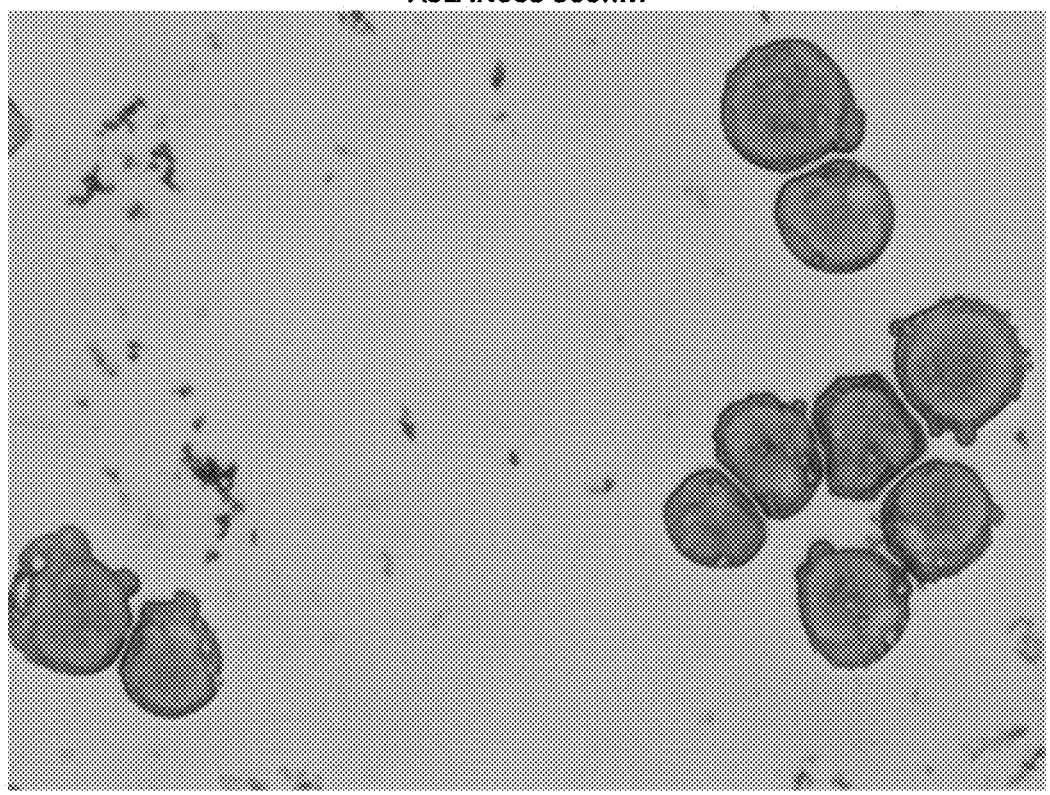
Figure 8:
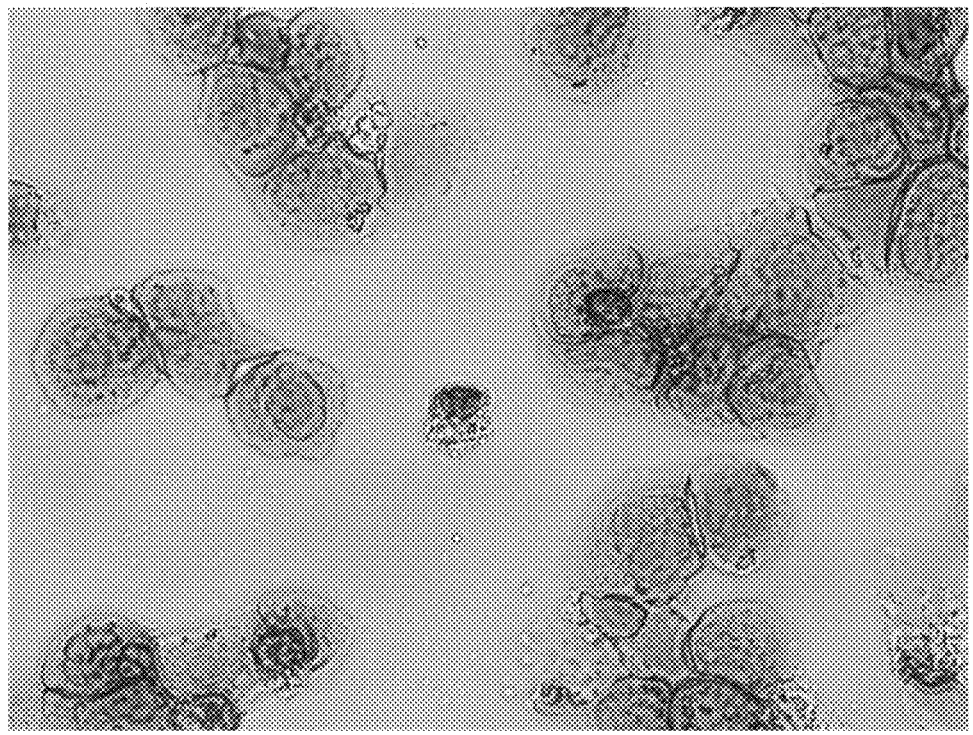
Figure 8:
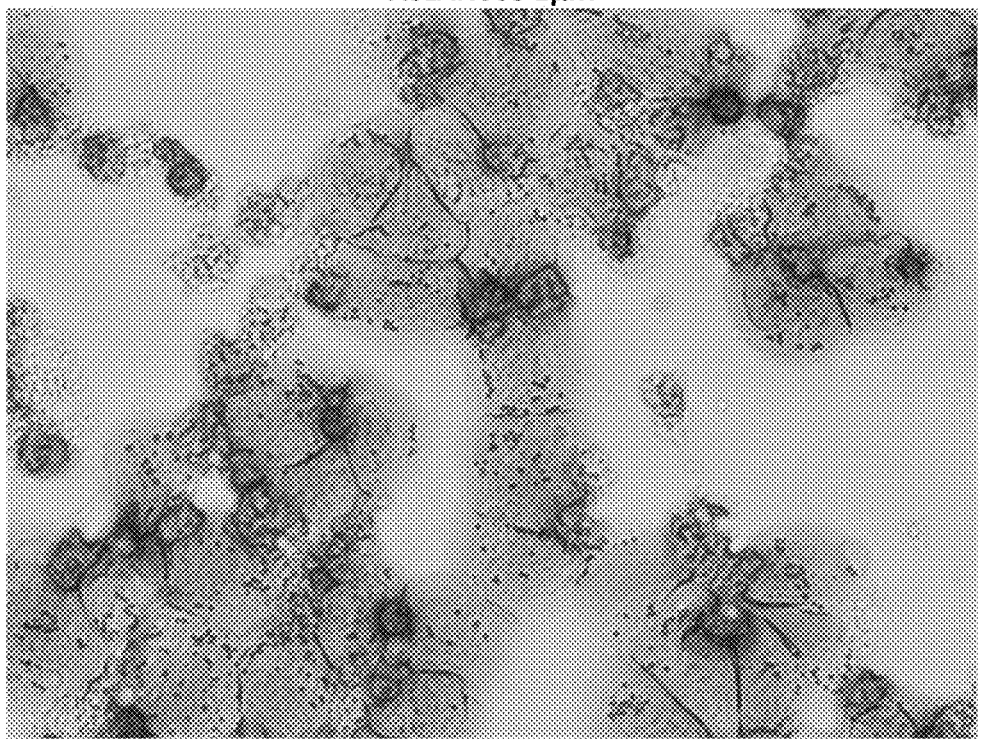
Figure 9:
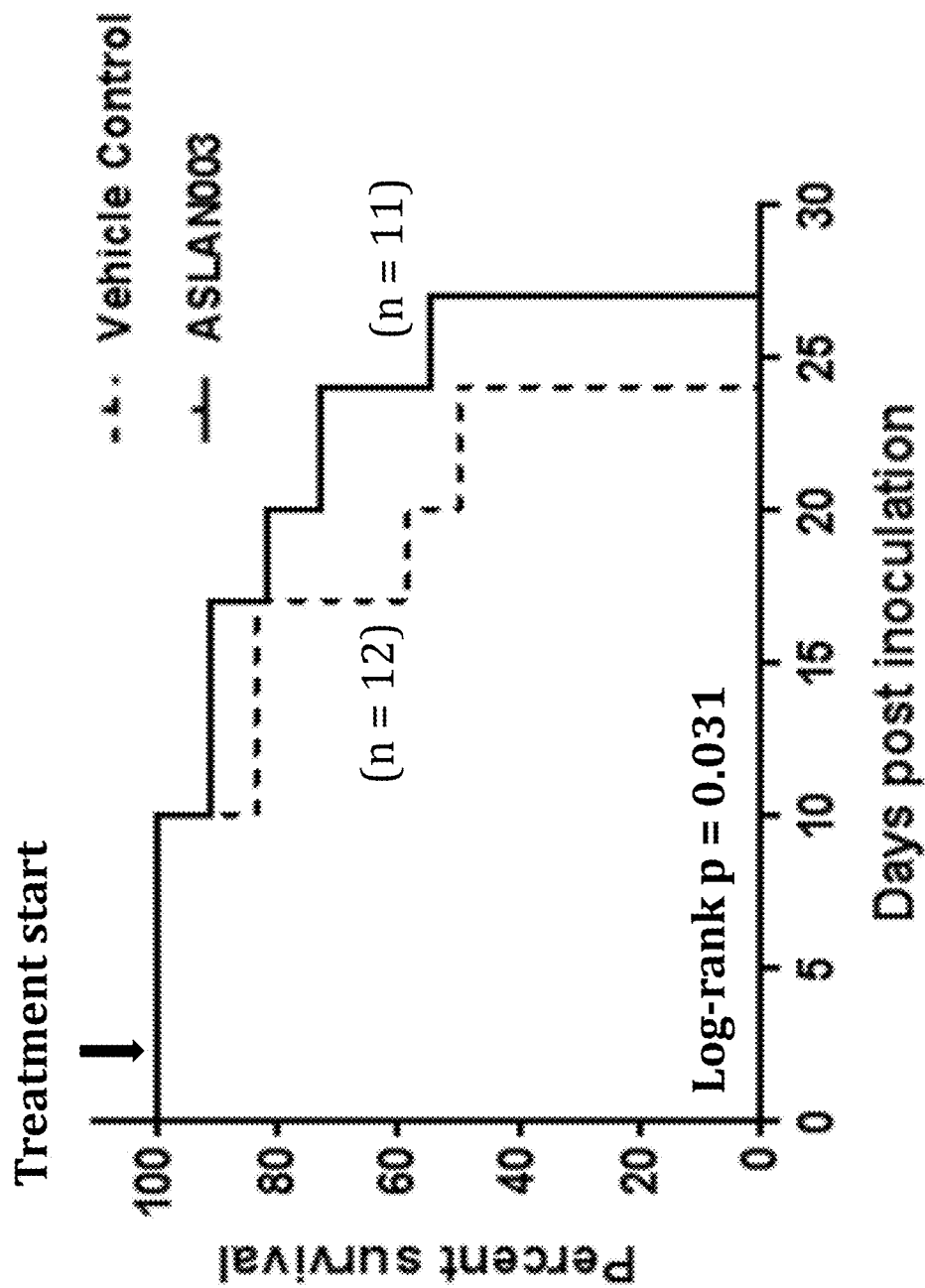
Figure 10:
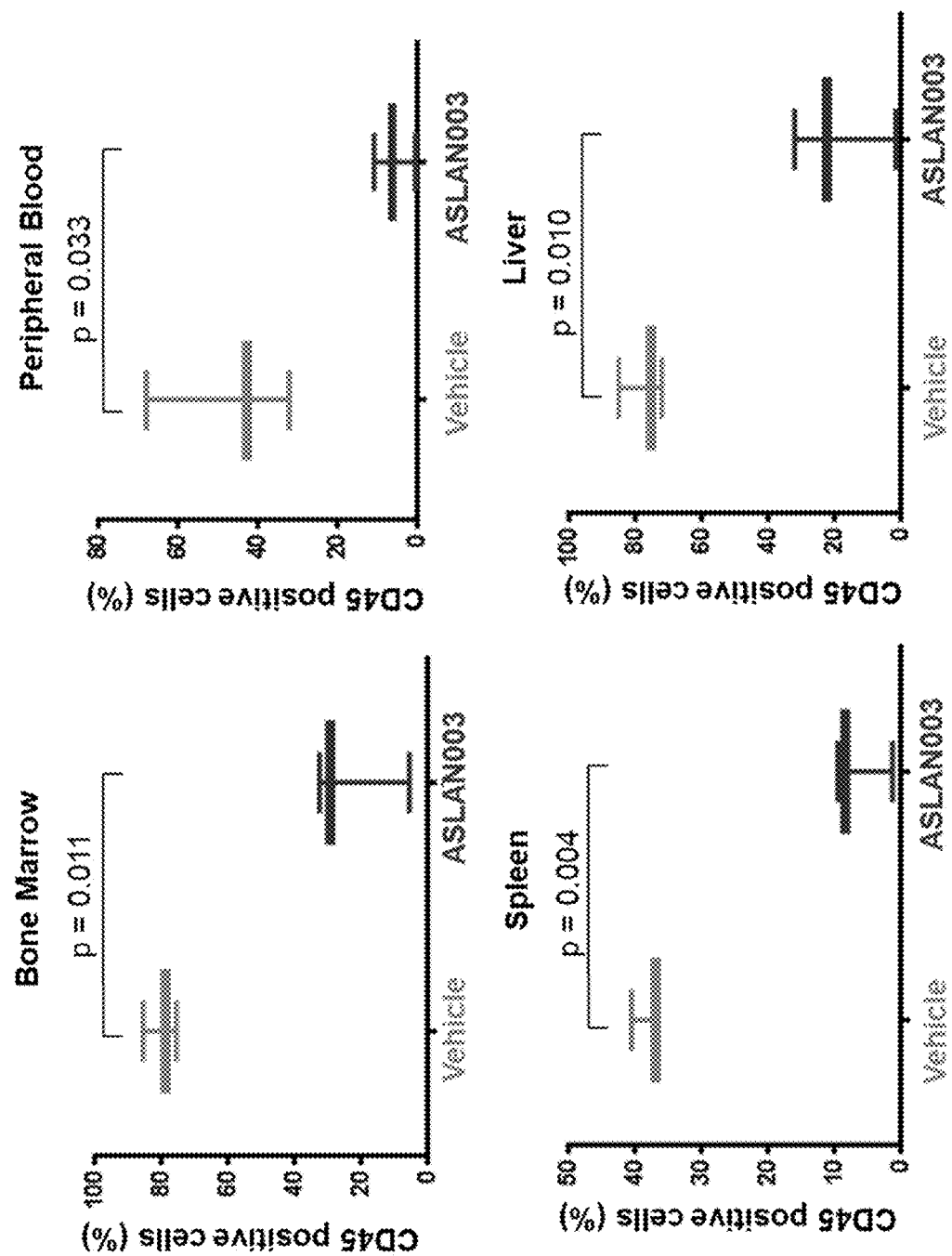
Figure 11:
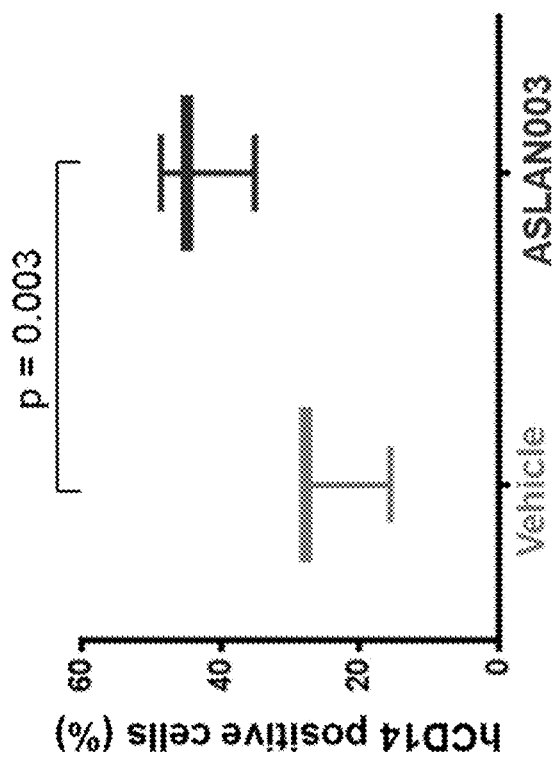
FIG. 11 Shows percentage of hCD11b+ cells in bone marrow of MOLM-14 xenograft mice following administration of ASLAN003
Figure 11:
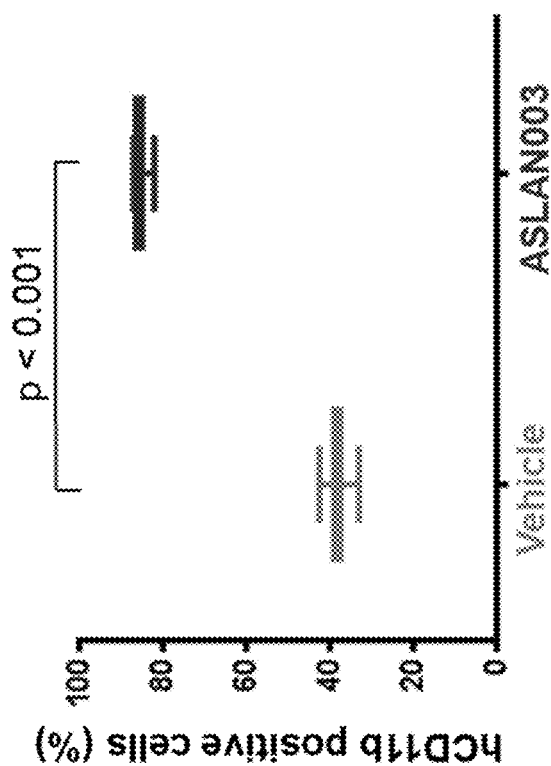

NSG mice were inoculated with MOLM-14 cells via tail vein injection. Treatment by oral gavage with either ASLAN003 (50 mg/kg QD) or vehicle control was started 3 days past inoculation. 11 mice were treated in the ASLAN003 group and 12 mice were treated in the vehicle control group. The following data is collected at the end of the experiment:

The results are shown in FIGS. 9 to 11.

FIG. 9 demonstrates that ASLAN003 significantly (p=0.031) prolonged survival of MOLM-14 xenograft mice—the median survival for the vehicle group was 24 days vs 27 days for the group treated with ASLAN003.

FIG. 10 shows the results of the flow cytometry analysis of CD45+ cells in the bone marrow, peripheral blood, spleen and liver of MOLM-14 xenograft mice. The percentage of CD45+ cells is an indication of leukaemic burden. Thus, FIG. 10 indicates that ASLAN003 significantly decreased leukaemic burden in the bone marrow, peripheral blood, spleen and liver of MOLM-14 xenograft mice.

FIG. 11 shows the results of the flow cytometry analysis of hCD11b+ and hCD14+ cells in the bone marrow of MOLM-14 xenograft mice. CD11b and CD14 are markers of cell differentiation. Thus, the results in FIG. 11 shows that ASLAN003 significantly induced differentiation of leukaemic cells in the bone marrow of MOLM-14 xenograft mice.

Taken together, the above studies clearly demonstrate that ASLAN003 was able to significantly prolong the survival, reduce the leukaemic burden and induce differentiation of leukaemic cells in an AML animal model.

EXAMPLE 3—AN IN VITRO ANALYSIS OF ASLAN003 CARRIED OUT ON AD345 AND AD537 MDS CELLS

AD345 primary MDS cells (refractory cytopenia with multilineage dysplasia, normal karyotype) and AD537 primary MDS bone marrow cells (refractory cytopenia with multilineage dysplasia, karyotype 46, XY, 43.1% myeloid) were treated with ASLAN003 (4000 nM) or DMSO control for 96 hours. A FACs analysis was then performed using Pacific blue dye. The AD537 cells were also stained with Wright-Giemsa and NBT reduction.

Figure 12:
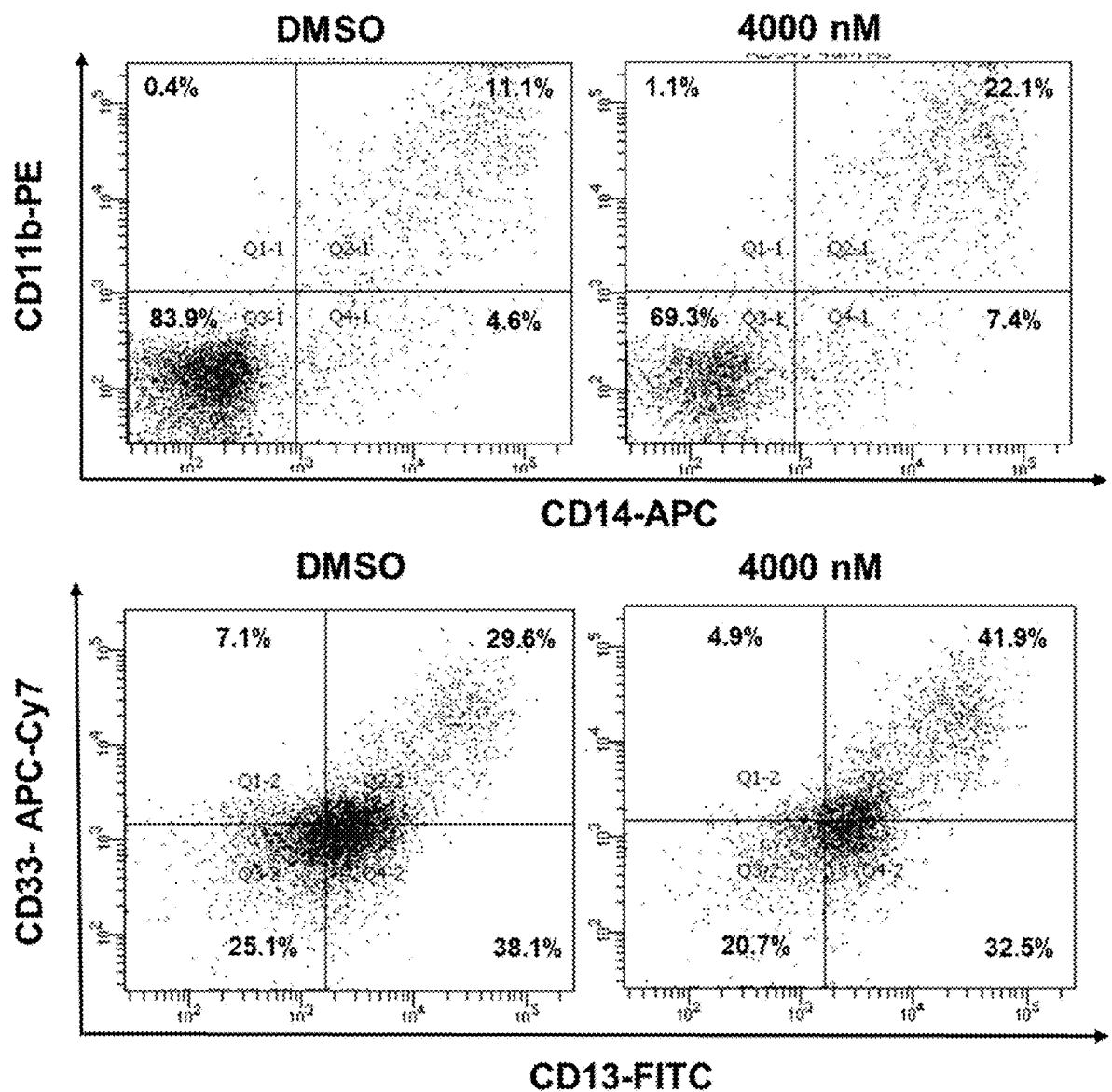
FIG. 12 Shows flow cytometry results for primary AD345 MDS cells after 96 hours treatment with ASLAN003.

FIG. 12 shows the results of the FACs analysis for the AD345 MDS cells. A reduction in % viable cells from 93% to 86.5% was observed between the AD345 cells treated with ASLAN003 vs DMSO control. We also observed an about 11% increase in CD11b+CD14+ cells in 4 µM ASLAN003 treated samples. CD13+CD33+ cells were increased about 12.3% in 4 µM ASLAN003 treated samples.

Figure 13:
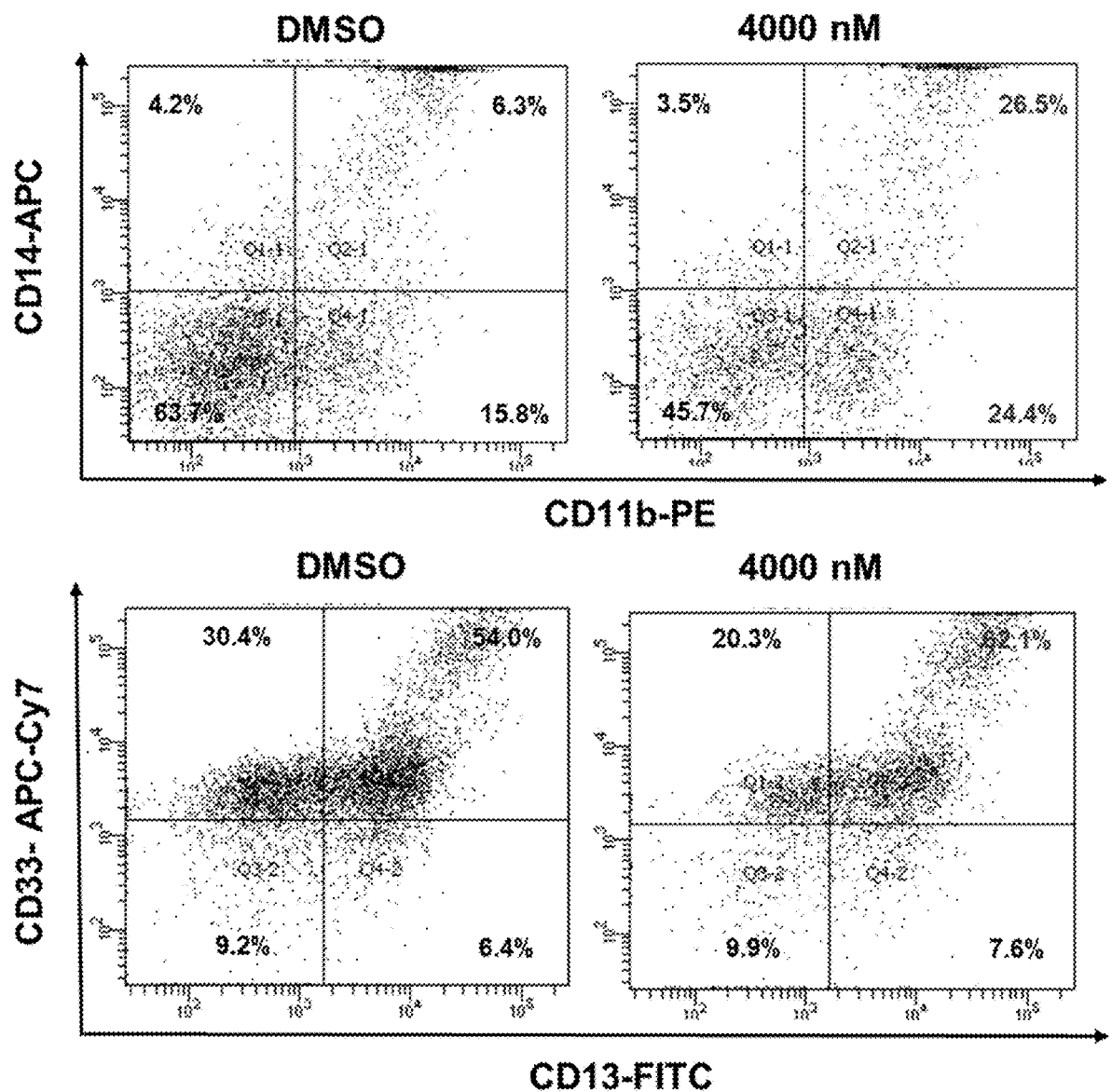
FIG. 13 Shows flow cytometry results for primary AD537 MDS cells after 96 hours treatment with ASLAN003.
Figure 14:
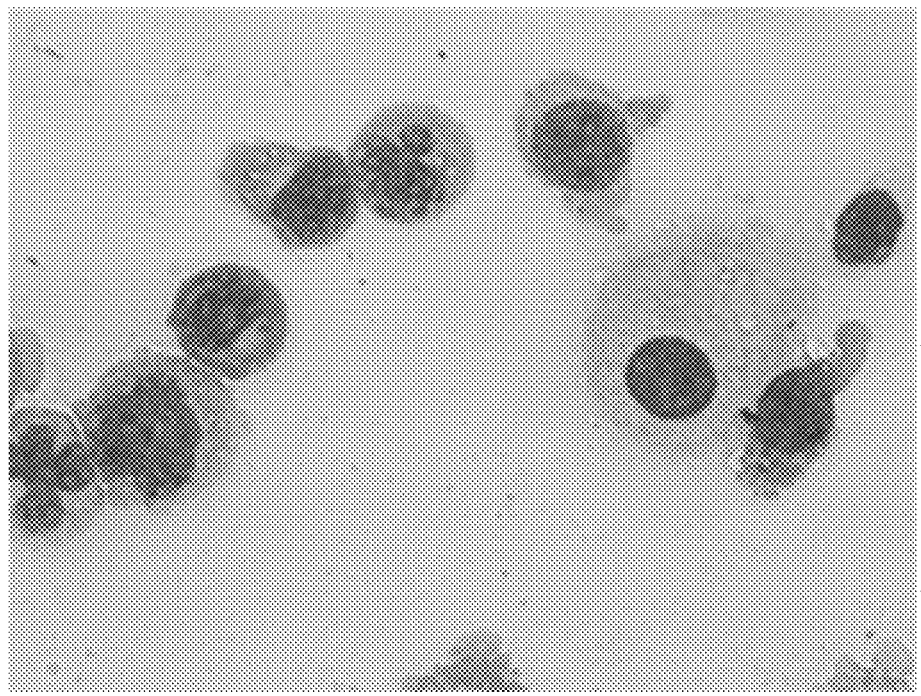
FIG. 14 Shows Wright-Giemsa Staining for AD537 cells.
Figure 14:
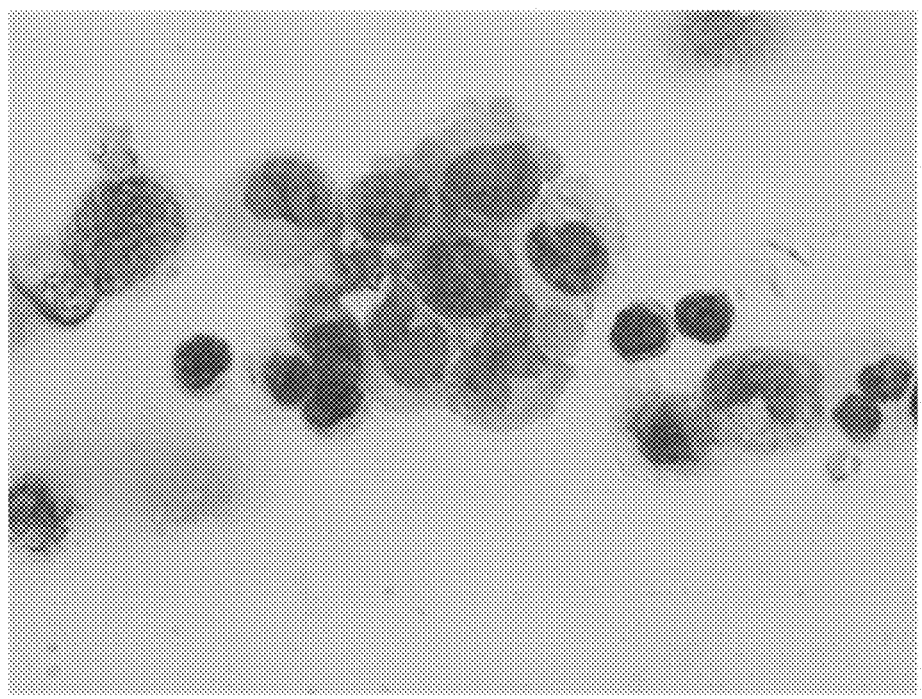
Figure 15:
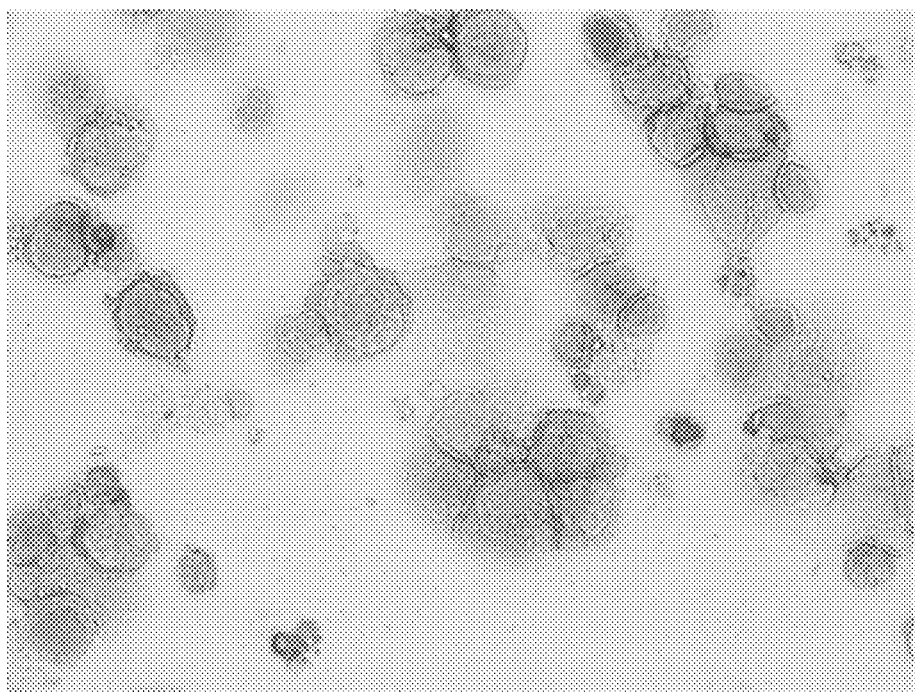
FIG. 15 Shows NBT reduction staining for AD537 cells.
Figure 15:
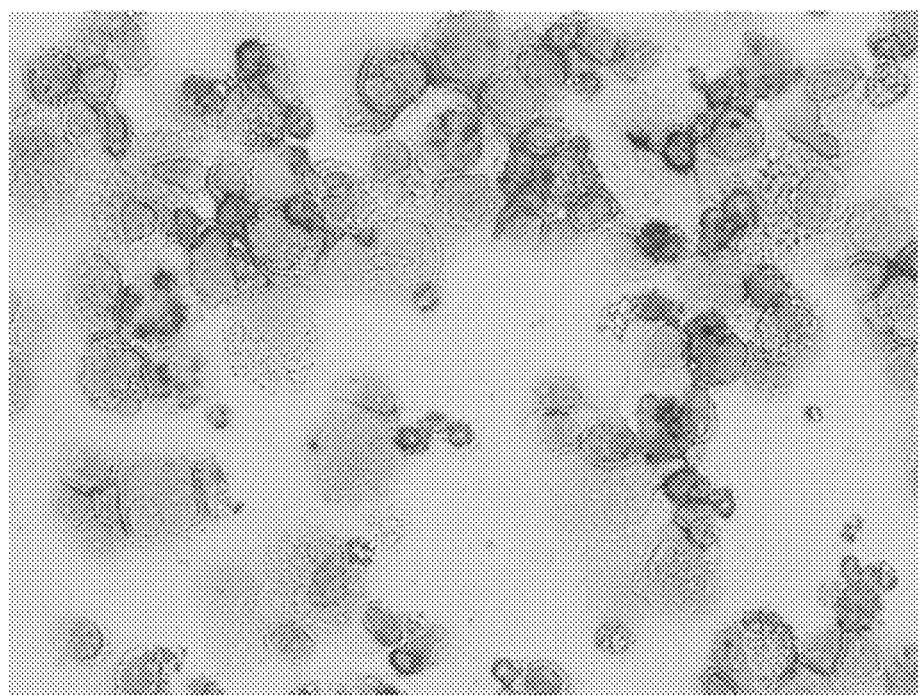

FIG. 13 shows the results of the FACs analysis for the AD537 MDS cells. A reduction in % viable cells from 84.5% to 73% was observed between the AD537 cells treated with ASLAN003 vs DMSO control. We also observed an about 20% increase in CD14+ cells and 30% increase of CD11b+ cells in 4 µM ASLAN003 treated samples. CD13+CD33+ cells were increased about 12.3% in 4 µM ASLAN003 treated samples.

These results thus suggest that ASLAN003 was able to reduce the viability of MDS cells, indicating the potential for ASLAN003 as a treatment for MDS.

The invention claimed is:

1. A method of treating a haematological cancer, comprising administering a DHODH inhibitor 2-(3,5-difluoro-3'methoxybiphenyl-4-ylamino)nicotinic acid or a pharmaceutically acceptable salt thereof to a patient in need thereof, wherein the cancer is acute myeloid leukaemia (AML) excluding acute promyelocytic leukaemia.

2. A method of treatment according to claim 1, wherein the DHODH inhibitor is employed in a combination therapy with a second therapy, wherein the second therapy is selected from an inhibitor of DNA repair, a PARP-1 inhibitor, a PARP-2 inhibitor, a topoisomerase I and/or a topoisomerase II inhibitor.

3. A method of treatment according to claim 2, wherein the second therapy is an inhibitor of DNA repair, wherein the inhibitor is selected from TRC102, (2E)-2-[(4,5-Dimethoxy-2-methyl-3,6-dioxo-1,4-cyclohexadien-1-yl)methylene]-undecanoic acid [also known as E3330], NCS-666715 and NSC-124854, 8-oxoguanine, tanespirmycin, luminespib, alvespimycin, genetespib, retaspimycin, 6-Amino-8-[(6-iodo-1,3-benzodioxol-5-yl)thio]-N-(1-methylethyl)-9H-purine-9-propanamine (PU-H71), 4-[2-carbamoyl-5-[6,6-dimethyl-4-oxo-3-(trifluoromethyl)-5,7-dihydroindazol-1-yl]anilino]cyclohexyl] 2-aminoacetate (SNX-5422), luminespib (resorcyinylic), 2-(2-ethyl-3,5-dihydroxy-6-(3-methoxy-4-(2-morpholinoethoxy)benzoyl)phenyl)-N,N-bis(2-methoxyethyl)acetamide (KW-2478), AT13387, 5,6-bis((E)-benzylideneamino)-2-thioxo-2,3-dihydropyrimidin-4(1H)-one (SCR7), 7-hydroxystaurosporine [UCN-01], trabectedin, MC113E, NER101 and combinations of two or more of the same.

4. A method of treatment according to claim 3, wherein the inhibitor mechanism is via the base excision repair pathway.

5. A method of treatment according to claim 3, wherein the inhibitor's target is independently selected from APE1, Pol β, FEN1, and PARP.

6. A method of treatment according to claim 2, wherein the second therapy is a PARP inhibitor independently selected from olaparib, rucaparib, niraparib, iniparib, talazoparib, veliparib, CEP9722, E7016, BGB-290, AZD-2461, 3-aminobenzamide and combinations thereof.

7. A method of treatment according to claim 3, wherein the inhibitor mechanism is via the mismatch repair pathway.

8. A method of treatment according to claim 3, wherein the inhibitor mechanism is via the nucleotide excision pathway.

9. A method of treatment according to claim 3, wherein the inhibitor is independently selected from 7-hydroxystaurosporine [UCN-01], trabectedin, MC113E, NER101 and combinations of two or more of the same.

10. A method of treatment according to claim 3, wherein the inhibitor mechanism is via the double stranded break repair pathway.

11. A method of treatment according to claim 3, wherein the inhibitor mechanism is via the non-homologous end joining pathway.

12. A method of treatment according to claim 3, wherein the inhibitor is via the homologous recombination pathway.

13. A method of treatment according to claim 2, wherein the therapy is a topoisomerase inhibitor independently selected from irinotecan, topotecan, camptothecin, lamellarin D, etoposide (VP-16), teniposide, doxorubicin, daunorubicin, mitoxantrone, amsacrine, ellipticines, aurintricarboxylic acid, 3-Hydroxy-2-[(1R)-6-isopropenyl-3-methylcyclohex-2-en-1-yl]-5-pentyl-1,4-benzoquinone (HU-331) and combinations thereof.

* * * * *